(12) United States Patent
Delaney et al.

(10) Patent No.: US 9,167,215 B2
(45) Date of Patent: *Oct. 20, 2015

(54) MACHINE VISION SYSTEM EDITING ENVIRONMENT FOR A PART PROGRAM IN WHICH A CONTINUOUS STREAM OF IMAGE ACQUISITION OPERATIONS ARE PERFORMED DURING A RUN MODE

(71) Applicant: Mitutoyo Corporation, Kawasaki-shi, Kanagawa-ken (JP)

(72) Inventors: Mark Delaney, Shoreline, WA (US); Barry E. Saylor, Kent, WA (US)

(73) Assignee: Mitutoyo Corporation, Kawasaki-shi (JP)

( * ) Notice: Subject to any disclaimer, the term of this patent is extended or adjusted under 35 U.S.C. 154(b) by 14 days.

This patent is subject to a terminal disclaimer.

(21) Appl. No.: 14/307,458

(22) Filed: Jun. 17, 2014

(65) Prior Publication Data

US 2014/0293077 A1    Oct. 2, 2014

Related U.S. Application Data

(63) Continuation-in-part of application No. 13/297,220, filed on Nov. 15, 2011, now Pat. No. 8,902,307.

(51) Int. Cl.
*H04N 7/18* (2006.01)
*H04N 5/232* (2006.01)
(Continued)

(52) U.S. Cl.
CPC ........... *H04N 7/183* (2013.01); *G01N 21/8806* (2013.01); *G02B 21/24* (2013.01); *G02B 21/365* (2013.01); *G05B 19/401* (2013.01); *G05B 19/4093* (2013.01); *G05B 19/42* (2013.01);
(Continued)

(58) Field of Classification Search
None
See application file for complete search history.

(56) References Cited

U.S. PATENT DOCUMENTS 4,835,730 A    5/1989 Shimano
5,481,712 A    1/1996 Silver
(Continued)

OTHER PUBLICATIONS

"QVPAK 3D CNC Vision Measuring Machine: Operation Guide," Version 2.0, Manual No. 4911GB, Series No. 359, Mitutoyo Corporation & Micro Encoder Inc., Kanagawa, Japan, Sep. 1996, 86 pages.
(Continued)

*Primary Examiner* — Joseph Ustaris
*Assistant Examiner* — William Adrovel
(74) *Attorney, Agent, or Firm* — Christensen O'Connor Johnson Kindness PLLC

(57) ABSTRACT

In a machine vision system editing environment for a part program, a continuous stream of image acquisition operations are performed during a run mode. Previously, a continuous stream of image acquisition operations was achieved by utilizing different programming representations and syntax for programming and grouping image acquisition operations together in the part program. A new common syntax and representations are utilized wherein such continuous image acquisition operations are recorded in the same way as regular operations, with the running of the part program being performed in two stages. First, the portion of the part program that is to have the continuous stream of image acquisition is scanned for image acquisition operations, and the most efficient order for acquiring the images is determined. Second, while the image acquisition process is being performed, the portion of the part program is scanned again, with the image analysis operations then being performed.

31 Claims, 9 Drawing Sheets

(51) Int. Cl.

| | | |
|---|---|---|
| *G02B 21/24* | (2006.01) | |
| *G02B 21/36* | (2006.01) | |
| *G01N 21/88* | (2006.01) | |
| *G05B 19/401* | (2006.01) | |
| *G05B 19/4093* | (2006.01) | |
| *G05B 19/42* | (2006.01) | |
| *G06T 1/00* | (2006.01) | |
| *G06F 9/06* | (2006.01) | |
| *G06F 9/44* | (2006.01) | |

(52) U.S. Cl.
CPC .......... *G06T 1/0007* (2013.01); *H04N 5/23203* (2013.01); *H04N 5/23209* (2013.01); *G01N 21/8851* (2013.01); *G06F 9/06* (2013.01); *G06F 9/4443* (2013.01); *H04N 5/232* (2013.01)

(56) References Cited

U.S. PATENT DOCUMENTS

| | | |
|---|---|---|
| 5,537,546 A | 7/1996 | Sauter |
| 6,016,467 A | 1/2000 | Newsted |
| 6,510,434 B1 | 1/2003 | Anderson |
| 6,542,180 B1 | 4/2003 | Wasserman |
| 6,636,211 B2 | 10/2003 | Chartier |
| 7,055,092 B2 | 5/2006 | Yardumian |
| 7,207,017 B1 | 4/2007 | Tabery |
| 7,324,682 B2 | 1/2008 | Wasserman |
| 7,376,904 B2 | 5/2008 | Cifra |
| 7,454,053 B2 | 11/2008 | Bryll |
| 7,590,276 B2 | 9/2009 | Delaney |
| 7,643,907 B2 | 1/2010 | Fuhlbrigge |
| 7,689,634 B2 | 3/2010 | Agarwal |
| 7,864,178 B2 | 1/2011 | Marini |
| 8,028,085 B2 | 9/2011 | Elien |
| 8,111,905 B2 | 2/2012 | Campbell |
| 8,111,938 B2 | 2/2012 | Bryll |
| 2006/0150148 A1 | 7/2006 | Beckett |
| 2006/0178778 A1 | 8/2006 | Fuhlbrigge |
| 2007/0067290 A1 | 3/2007 | Makela |
| 2007/0150102 A1 | 6/2007 | Park |
| 2007/0250204 A1 | 10/2007 | Ould |
| 2009/0164020 A1 | 6/2009 | Janowski |
| 2010/0103679 A1 | 4/2010 | Lee |
| 2010/0158343 A1 | 6/2010 | Bryll |
| 2010/0269094 A1 | 10/2010 | Levenshteyn |
| 2011/0103679 A1 | 5/2011 | Campbell |
| 2013/0120567 A1 | 5/2013 | Northrup |
| 2013/0123945 A1 | 5/2013 | Saylor |

OTHER PUBLICATIONS

"QVPAK 3D CNC Vision Measuring Machine: User's Guide," Version 7.1, 2d ed., Manual No. 99MCB225A, Series No. 359, Mitutoyo Corporation & Micro Encoder Inc., Kanagawa, Japan, Sep. 2003, 370 pages.

Saylor, B., et al., "Machine Vision System Program Editing Environment Including Synchronized User Interface Features," U.S. Appl. No. 61/560,278, filed Nov. 15, 2011.

MACHINE VISION SYSTEM EDITING ENVIRONMENT FOR A PART PROGRAM IN WHICH A CONTINUOUS STREAM OF IMAGE ACQUISITION OPERATIONS ARE PERFORMED DURING A RUN MODE

CROSS-REFERENCE TO RELATED APPLICATION

This application is a continuation-in-part of U.S. patent application Ser. No. 13/297,220, filed Nov. 15, 2011, the disclosure of which is incorporated by reference herein in its entirety.

FIELD OF THE INVENTION

The present disclosure relates generally to machine vision inspection systems, and more particularly to editing environments for part programs that include continuous high-speed image acquisition in such systems.

BACKGROUND

Precision machine vision inspection systems (or "vision systems" for short) can be utilized to obtain precise dimensional measurements of inspected objects and to inspect various other object characteristics. Such systems may include a computer, a camera and optical system, and a precision stage that is movable in multiple directions so as to allow the camera to scan the features of a workpiece that is being inspected. One exemplary prior art system that is commercially available is the QUICK VISION® series of PC-based vision systems and QVPAK® software available from Mitutoyo America Corporation (MAC), located in Aurora, Ill. The features and operation of the QUICK VISION® series of vision systems and the QVPAK® software are generally described, for example, in the *QVPAK 3D CNC Vision Measuring Machine User's Guide*, published January 2003, and the *QVPAK 3D CNC Vision Measuring Machine Operation Guide*, published September 1996, each of which is hereby incorporated by reference in their entirety. This product, as exemplified by the QV-302 Pro model, for example, is able to use a microscope-type optical system to provide images of a workpiece at various magnifications, and move the stage as necessary to traverse the workpiece surface beyond the limits of any single video image. A single video image typically encompasses only a portion of the workpiece being observed or inspected, given the desired magnification, measurement resolution, and physical size limitations of such systems.

Machine vision inspection systems generally utilize automated video inspection. U.S. Pat. No. 6,542,180 teaches various aspects of such automated video inspection and is incorporated herein by reference in its entirety. As taught in the '180 patent, automated video inspection metrology instruments generally have a programming capability that allows an automatic inspection event sequence to be defined by the user for each particular workpiece configuration. This can be implemented by text-based programming, for example, or through a recording mode that progressively "learns" the inspection event sequence by storing a sequence of machine control instructions corresponding to a sequence of inspection operations performed by a user with the aid of a graphical user interface, or through a combination of both methods. Such a recording mode is often referred to as "learn mode" or "training mode." Once the inspection event sequence is defined in "learn mode," such a sequence can then be used to automatically acquire (and additionally analyze or inspect) images of a workpiece during "run mode."

Video tools (or "tools" for short) and other graphical user interface features may be used manually to accomplish manual inspection and/or machine control operations (in "manual mode"). Their set-up parameters and operation can also be recorded during learn mode, in order to create automatic inspection programs, or "part programs." Video tools may include, for example, edge/boundary detection tools, autofocus tools, shape or pattern matching tools, dimension measuring tools, and the like. Other graphical user interface features may include dialog boxes related to data analysis, step and repeat loop programming, and the like. For example, such tools are routinely used in a variety of commercially available machine vision inspection systems, such as the QUICK VISION® series of vision systems and the associated QVPAK® software, discussed above.

The machine control instructions including the specific inspection event sequence (i.e., how to acquire each image and how to analyze/inspect each acquired image) are generally stored as a "part program" or "workpiece program" that is specific to the particular workpiece configuration. For example, a part program defines how to acquire each image, such as how to position the camera relative to the workpiece, at what lighting level, at what magnification level, etc. Further, the part program defines how to analyze/inspect an acquired image, for example, by using one or more video tools such as edge/boundary detection video tools. The ability to create part programs with instructions that perform a predetermined sequence of inspection operations provides several benefits, including enhanced inspection repeatability, as well as the ability to automatically execute the same part program repeatedly on one or more compatible machine vision inspection systems.

For general-purpose machine vision inspection systems that are intended to be rapidly programmable for a wide variety of workpieces, as exemplified by the previously referenced QUICK VISION® series of PC-based vision systems, it has been conventional for image acquisition operations to be interspersed with image analysis operations and/or feature inspection operations that are performed on the most recently acquired image (referred to herein as "interspersed" type operations). However, there is an increasing demand for general-purpose machine vision inspection systems to provide higher throughput. According to one method, this may be accomplished by performing image acquisition while using continuous relative motion between the camera and the workpiece stage (as opposed to intermittently stopping and starting the relative motion, as required for interspersed type operations), thereby significantly increasing inspection throughput. Such operations are referred to herein as continuous-motion type operations. It is advantageous for such systems to include strobe lighting illumination to assist with the acquisition of images during continuous motion without smearing (or blurring) the image.

High-speed "in-line" vision inspection systems used in high-speed production lines have provided continuous-motion type image acquisition. However, such in-line vision systems typically are dedicated to a single production line and acquire the "same" image over and over again, for successive workpieces on a conveyor system, for example. In such cases, for each image the motion speed and strobe illumination parameters, etc., are the same. Furthermore, workpiece configurations and/or image acquisition parameters, etc., are rarely changed. Thus, programming methods for such systems have not facilitated rapid programming for an unlimited variety of workpieces, camera positions, image acquisition parameters, etc., by relatively unskilled users.

In contrast, experience has shown that it is essential for general-purpose machine vision inspection systems to facilitate rapid programming for an unlimited variety of workpieces, camera positions, image acquisition parameters, etc., by relatively unskilled users. Previous programming methods for general-purpose machine vision inspection systems have not made the programming of continuous-motion type operations sufficiently easy or fast. Furthermore, previous programming methods have not made the programming of continuous-motion type operations in combination with interspersed-type operations sufficiently easy or fast. Programming systems and methods that can overcome these problems and shortcomings, either separately or in combination, would be desirable.

One exemplary prior art method that overcomes some of these problems and shortcomings is illustrated in U.S. Pat. No. 7,590,276, which is hereby incorporated by reference in its entirety. As described in the '276 patent, a method of part programming is provided, which permits a user to readily define multiple image acquisition operations interspersed with associated image analysis operations during learn mode operations, in a natural and intuitively understandable relationship. Then, in the resulting part program, image acquisition operations for at least some of the images are automatically rearranged into a continuous motion image acquisition sequence that acquires images and stores images in a "non-interspersed" manner in order to increase the throughput of the machine vision inspection system.

However, one drawback of certain previous programming methods, such as that illustrated in the '276 patent, is that the continuous stream of image acquisition operations has typically been achieved by analyzing various operations entered by the user during learn mode, and altering or "regrouping" their order in the part program instructions using "regrouped" programming representations and syntax such that the image acquisition instructions are grouped together for acquiring a plurality of images using continuous motion, and their corresponding image analysis instructions are altered or "regrouped" to follow the image acquisition instructions, such that the image analysis operations need not be interspersed with or interrupt the high-speed image acquisition during the continuous motion. As a result, when the part program instructions are recalled for editing or viewing, the image analysis instructions are separated from the acquisition instructions for their corresponding image. This has proven to be confusing for the users of such systems, in that related image acquisition and analysis instructions are separated by intervening "unrelated" image acquisition and image processing instructions, which is non-intuitive, and leads to inefficiencies and errors when a user attempts to read or edit the "rearranged" part program instructions. In other words, the rearranged programming representations and syntax for grouping the image acquisition operations together in the part program have made programming and editing of such part programs more difficult for users. A need exists for a part programming syntax, and editing operations and features that overcome these and other deficiencies to allow more efficient, intuitive, and flexible programming and editing of continuous image acquisition part programs for precision machine vision inspection systems.

SUMMARY

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

In various embodiments, a precision machine vision system editing environment is provided for a part program in which a continuous or uninterrupted sequential stream of image acquisition operations is performed during a run mode. The precision machine vision inspection system includes an imaging portion, a stage for holding one or more workpieces in a field of view (FOV) of the imaging portion, a control portion, a display, and a user interface.

In various embodiments, the machine vision inspection system further comprises a learn mode that is operable to receive user input to control operations of the machine vision inspection system and record instructions corresponding to the controlled operations in order to create a part program. The learn mode is also operable to edit the part program, and to execute previously recorded part program instructions according to an edit mode of execution. In some embodiments, the learn mode may include user interface features such as a user-controllable stream mode instruction element and an editable part program representation of part program instructions. The user-controllable stream mode instruction element may be usable to designate a stream mode segment that comprises a segment of a part program that is designated for stream mode execution. In various embodiments, stream mode execution may comprise performing image acquisition operations in a sequential order during a continuous motion sequence wherein the stage and the imaging portion move continuously, or approximately continuously, relative to one another for acquiring at least two images. The editable part program representation includes image acquisition instruction representations corresponding to image acquisition operations, image analysis instruction representations corresponding to image analysis operations, and may include a stream mode segment representation, in some embodiments.

In various embodiments, the machine vision inspection system comprises a run mode that is operable to execute a previously created part program. The run mode generally comprises a stream mode of execution for executing at least some of the part program instructions. In some embodiments wherein stream mode segments are defined in a part program, the run mode may comprise a nonstream mode for executing part program instructions that are not in a defined stream mode segment, as well as the stream mode for executing part program instructions that are in a defined stream mode segment. In some embodiments, the nonstream mode of execution executes the image acquisition instructions and corresponding image analysis instructions of the first plurality of part program instructions that are not in a stream mode segment to perform the image acquisition operations and corresponding image analysis operations in a manner that is consistent with the first order.

In various embodiments, the learn mode is configured such that the editable part program representation represents a first plurality of part program instructions comprising image acquisition and corresponding image analysis instructions in a first order corresponding to an order in which the corresponding controlled operations were performed to create the part program. In addition, the learn mode is further configured such that the edit mode of execution executes the part program image acquisition instructions and corresponding image analysis instructions of the first plurality of part program instructions to perform the image acquisition operations and corresponding image analysis operations in a manner that is consistent with the first order, regardless of whether or not the first plurality of part program image acquisition and corresponding image analysis instructions are included in a stream mode segment (if defined).

In various embodiments, the run mode is configured such that the stream mode executes the first plurality of part program image acquisition and corresponding image analysis instructions according to a second order (e.g., by default, or in some embodiments, when they are included in a defined stream mode segment). In one embodiment, the second order includes performing the first plurality of part program image acquisition instructions to perform their corresponding image acquisition operations in a sequential order without dependence on performing the corresponding image analysis operations. In addition, the second order may further include performing the first plurality of part program image analysis instructions to perform their corresponding image analysis operations after their corresponding images are acquired. In one embodiment, the performance of the image analysis operations after their corresponding images are acquired is done during the sequential order of image acquisition operations.

In some embodiments wherein the machine vision inspection system includes strobe illumination or other means to allow fast image exposure without blur, the performance of the image acquisition operations in a sequential order is done during a truly continuous motion sequence wherein the stage and the imaging portion move continuously relative to one another (e.g., the stage moves continuously relative to the imaging portion). In some configurations, stage motion may be operable to physically move a workpiece in a horizontal plane (e.g., an X-Y plane) but not move the imaging portion, whereas the stage motion may be operable to move the imaging portion in a vertical direction (e.g., a Z direction), but not the workpiece. In other configurations, stage motion may be operable to physically move a workpiece in one horizontal direction (e.g., an X direction) but not the imaging portion, whereas the stage motion may be operable to move the imaging portion in a different horizontal direction (e.g., a Y direction) and a vertical direction (e.g., a Z direction), but not the workpiece. In various embodiments, the image acquisition operations are performed in a continuous motion sequence for at least two images. In other embodiments wherein the machine vision inspection system lacks strobe illumination, or otherwise requires slowing or momentarily stopping the relative motion to limit image blur, the performance of the image acquisition operations in the sequential order may be done during an approximately continuous motion sequence. The approximately continuous motion sequence may include motion operations that prevent image blur (e.g., slowing or momentarily stopping the otherwise continuous motion as dictated by image acquisition requirements), but does not include motion delays related to performing image analysis, or the like.

In various embodiments, the performance of the image analysis operations after their corresponding images are acquired is performed at least partly during the sequential order of image acquisition operations.

In some embodiments, the learn mode is configured such that when a part program, including a stream mode segment, is recalled for editing, the editable part program representation is displayed in the first order, and the edit mode of execution executes the image acquisition operations and corresponding image analysis operations in a manner that is consistent with the first order. In accordance with another aspect of the present disclosure, the learn mode is configured such that a user may select a part program instruction representation included in a stream mode segment as a place to initiate edit mode of execution of corresponding part program instructions, after which subsequent part program instructions are executed in a manner that is consistent with the first order. In accordance with another aspect of the present disclosure, the subsequent part program instructions are executed in a manner that is consistent with the first order.

In some embodiments, the stream mode segment comprises a first set of instructions and a second set of instructions, the first set of instructions comprising first image acquisition instructions and first image analysis instructions that comprise video tool instructions of a first video tool, and the second set of instructions comprising second image acquisition instructions and second image analysis instructions that comprise video tool instructions of a second video tool, wherein during the edit mode of execution the first image acquisition instructions and first image analysis instructions that comprise video tool instructions of a first video tool are executed before beginning execution of the second image acquisition instructions and the second image analysis instructions that comprise video tool instructions of the second video tool. During the run mode, the stream mode segment is executed in the stream mode due to the stream mode instruction element, and during the run mode of execution executing of the stream mode segment, the first and second image acquisition instructions are executed in a sequential order without dependence on performing the corresponding first and second image analysis operations that comprise video tool instructions of the first and second video tool. In accordance with another aspect of the present disclosure, the first and second video tools comprise edge detection video tools.

In some embodiments, the part program further comprises a nonstream mode segment, and during the learn mode the nonstream mode segment is differentiated from the stream mode segment by the lack of a stream mode instruction element for the nonstream mode segment, the nonstream mode segment comprising a third set of instructions and a fourth set of instructions, the third set of instructions comprising third image acquisition instructions and third image analysis instructions that comprise video tool instructions of a third video tool, and the fourth set of instructions comprising fourth image acquisition instructions and fourth image analysis instructions that comprise video tool instructions of a fourth video tool, wherein during the edit mode of execution the third image acquisition instructions and third image analysis instructions that comprise video tool instructions of the third video tool are executed before beginning execution of the fourth image acquisition instructions and the fourth image analysis instructions that comprise video tool instructions of the fourth video tool. During the run mode, the nonstream mode segment is executed in the nonstream mode due to the lack of a stream mode instruction element for the nonstream mode segment, and during the run mode execution of the nonstream mode segment, the third and fourth image acquisition instructions are executed in a sequential order without dependence on performing the corresponding third and fourth image analysis operations that comprise video tool instructions of the third and fourth video tool.

In some embodiments, when a part program including a stream mode segment is recalled for editing, the editable part program representation is displayed in the first order, and the edit mode of execution executes the image acquisition operations and corresponding image analysis operations in a manner that is consistent with the first order.

In some embodiments, during the learn mode, a user may select any part program instruction in a stream mode segment as a place to start the execution of the part program instructions, after which the subsequent part program instructions are executed in a manner that is consistent with the first order.

In some embodiments, the stream mode segment comprises a first set of instructions and a second set of instructions. The first set of instructions includes first image acquisition instructions and first image analysis instructions that comprise video tool instructions of a first video tool, while the second set of instructions include second image acquisition instructions and second image analysis instructions that comprise video tool instructions of a second video tool. In one embodiment, during the edit mode of execution, first image acquisition instructions and first image analysis instructions that comprise video tool instructions of the first video tool are executed before beginning execution of the second image acquisition instructions and the second image analysis instructions which comprise video tool instructions of the second video tool. Then, during the run mode, the stream mode segment is executed in the stream mode due to the stream mode instruction element. During the run mode of execution of the stream mode segment, the first and second image acquisition instructions are executed in a sequential order without dependence on performing the corresponding first and second image analysis operations that comprise video tool instructions of the first and second video tool. In one embodiment, the first and second video tools comprise edge detection video tools.

In some embodiments, the part program further comprises a nonstream mode segment, and during the learn mode the nonstream mode segment is differentiated from the stream mode segment by the lack of a stream mode instruction element for the nonstream mode segment. In one embodiment, the nonstream mode segment includes a third set of instructions and a fourth set of instructions. The third set of instructions includes third image acquisition instructions and third image analysis instructions that comprise video tool instructions of a third video tool, while the fourth set of instructions includes fourth image acquisition instructions and fourth image analysis instructions that comprise video tool instructions of a fourth video tool. During the edit mode of execution, the third image acquisition instructions and third image analysis instructions that comprise video tool instructions of the third video tool are executed before beginning execution of the fourth image acquisition instructions and the fourth image analysis instructions that comprise video tool instructions of the fourth video tool. Then, during the run mode, the nonstream mode segment is executed in the nonstream mode due to the lack of a stream mode instruction element for the nonstream mode segment. During the run mode execution of the nonstream mode segment, the third and fourth image acquisition instructions are executed in a sequential order without dependence on performing the corresponding third and fourth image analysis operations that comprise video tool instructions of the third and fourth video tool.

In some embodiments, during the learn mode, the first and second sets of instructions are executed in the first order wherein at least some of the first and second image acquisition instructions are interspersed with the video tool instructions of the first video tool and the second video tool, the instructions being displayed on the user interface in the first order. Then, during the run mode, in the stream mode the part program instruction corresponding to the stream mode segment is processed to determine an image acquisition routine that comprises the image acquisition instructions of the first and second sets of instructions but not the video tool instructions, the image acquisition routine is executed for acquiring the images, and while the image acquisition routine is being executed, the video tool instructions are executed.

In some embodiments, during the run mode, in the stream mode at least a portion of the execution of the video tool instructions during the second time through the stream mode segment is done in parallel with the execution of the image acquisition routine.

In some embodiments, during the run mode, during the execution of the image acquisition routine, a plurality of the image acquisition instructions are executed in series during which time any video tool instructions that were interspersed during the learn mode are not yet executed, such that the instructions are executed in the second order that is different from the first order.

In some embodiments, during the run mode, when the image acquisition routine is executed, the stage and the imaging portion move continuously relative to one another for acquiring the images.

In some embodiments, the stream mode segment of the part program is identified by specified stream mode instruction representations at the beginning and end of the stream mode segment.

In some embodiments, during the learn mode, the part program instructions within the stream mode segment that are displayed in a part program representation are made to have an identical appearance to similar part program instructions that are outside of the stream mode segment, such that a user is not required to use a different programming representation or syntax when programming or editing operations that are inside of the stream mode segment as opposed to outside of the stream mode segment.

Although the previous summary has emphasized embodiments that include explicit stream mode segment marking or indication, stream mode segment marking and/or recognition of a separate mode or stream of operations may be incomprehensible or irrelevant to some users. For example, stream mode execution may be available on all machines possessed by a user and/or may be the default or only mode of execution used for run mode execution on a machine, so there may be no need to distinguish stream mode operation(s) for special recognition or consideration. In some embodiments, some or all stream mode compatible instructions and/or operations may be automatically executed in stream mode during run mode. In some implementations, this may be the default or only setting for run mode execution. In other implementations, the user may select either stream or nonstream mode execution as the global "automatic" mode of execution during run mode.

In any case, it should be appreciated that regardless of whether stream mode instructions are explicitly marked in a user interface or defined in a part program to indicate stream mode execution during run mode, many or all of the previously described features and benefits of nonstream edit mode representation and execution remain desirable and advantageous for users during learn mode and/or editing operations, as described in greater detail with reference to FIGS. 6A, 6B, and 7, below.

DESCRIPTION OF THE DRAWINGS

The foregoing aspects and many of the attendant advantages of the present disclosure will become more readily appreciated as the same become better understood by reference to the following detailed description, when taken in conjunction with the accompanying drawings, wherein.

DETAILED DESCRIPTION

Figure 1:
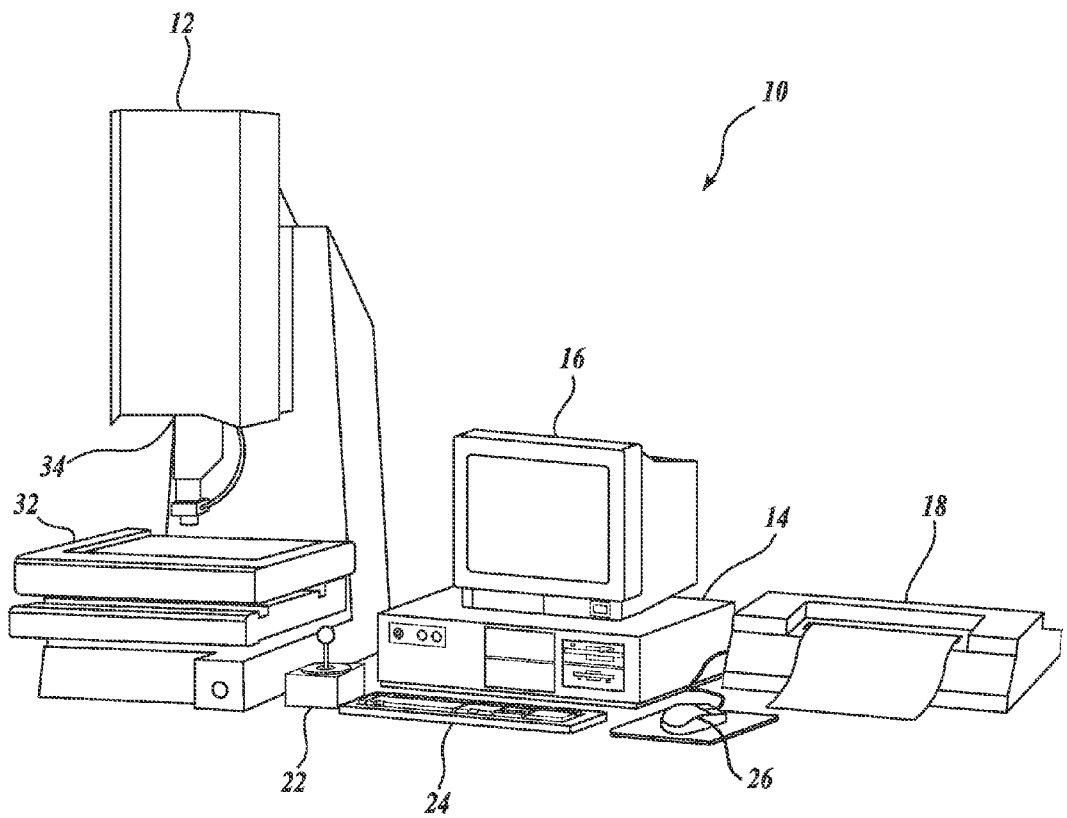
FIG. 1 is a diagram showing various typical components of a general purpose precision machine vision inspection system.

FIG. 1 is a block diagram of one exemplary machine vision inspection system 10 usable in accordance with the methods described herein. The machine vision inspection system 10 includes a vision measuring machine 12 that is operably connected to exchange data and control signals with a controlling computer system 14. The controlling computer system 14 is further operably connected to exchange data and control signals with a monitor or display 16, a printer 18, a joystick 22, a keyboard 24, and a mouse 26. The monitor or display 16 may display a user interface suitable for controlling and/or programming the operations of the machine vision inspection system 10.

The vision measuring machine 12 includes a moveable workpiece stage 32 and an optical imaging system 34 that may include a zoom lens or interchangeable lenses. The zoom lens or interchangeable lenses generally provide various magnifications for the images provided by the optical imaging system 34. The machine vision inspection system 10 is generally comparable to the QUICK VISION® series of vision systems and the QVPAK® software discussed above, and similar state-of-the-art commercially available precision machine vision inspection systems. The machine vision inspection system 10 is also described in commonly assigned U.S. Pat. Nos. 7,454,053, 7,324,682, 8,111,938, and 8,111,905, which are each incorporated herein by reference in their entireties.

Figure 2:
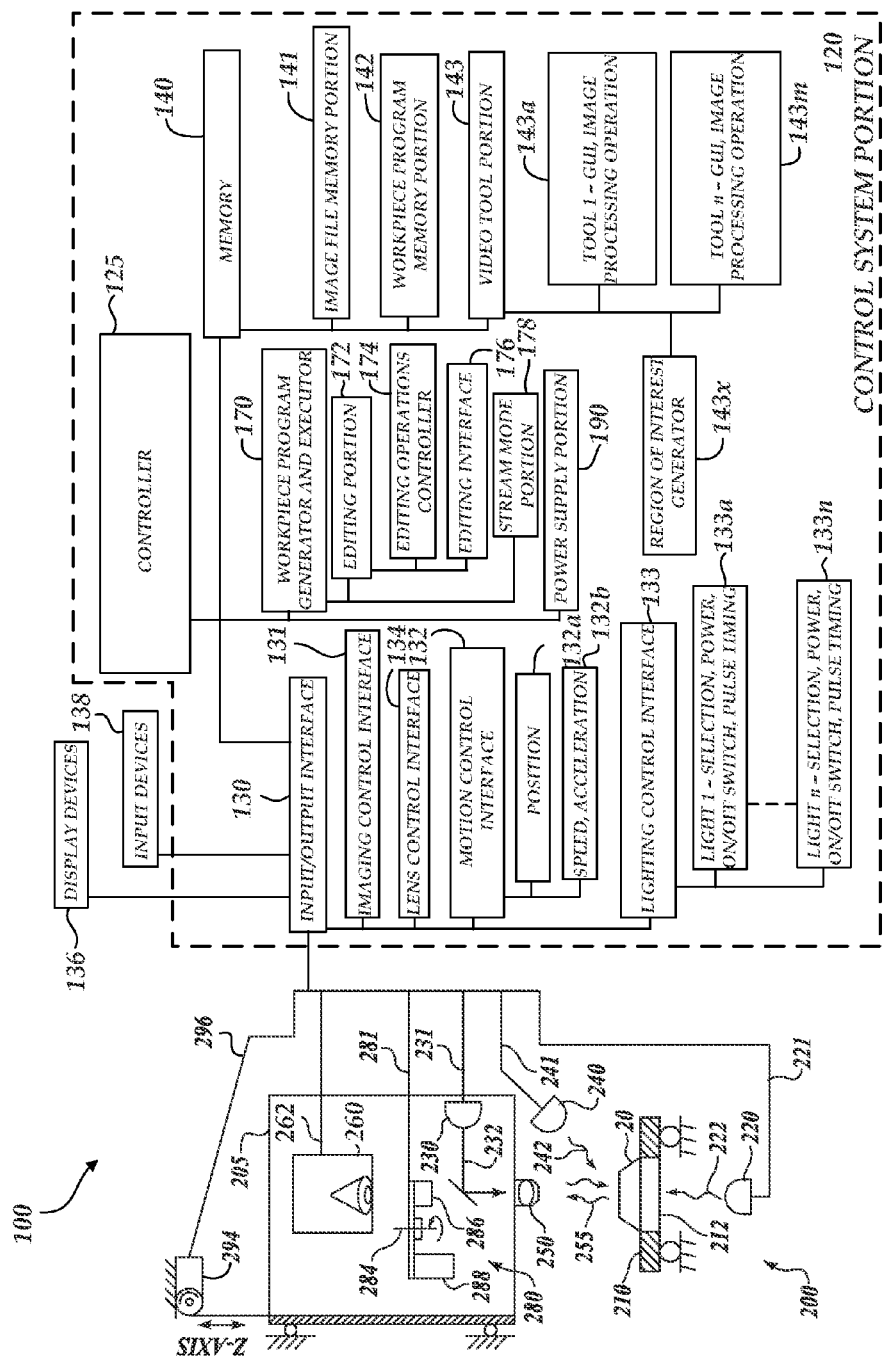
FIG. 2 is a block diagram of a control system portion and a vision components portion of a machine vision inspection system similar to that of FIG. 1, and including features according to the present disclosure.

FIG. 2 is a block diagram of a control system portion 120 and a vision components portion 200 of a machine vision inspection system 100 similar to the machine vision inspection system of FIG. 1, and including features according to the present disclosure. As will be described in more detail below, the control system portion 120 is utilized to control the vision components portion 200. The vision components portion 200 includes an optical assembly portion 205, light sources 220, 230, and 240, and a workpiece stage 210 having a central transparent portion 212. The workpiece stage 210 is controllably movable along X and Y axes that lie in a plane that is generally parallel to the surface of the stage where a workpiece 20 may be positioned. The optical assembly portion 205 includes a camera system 260, an interchangeable objective lens 250, and may include a turret lens assembly 280 having lenses 286 and 288. Alternatively to the turret lens assembly, a fixed or manually interchangeable magnification-altering lens, or a zoom lens configuration, or the like, may be included. The optical assembly portion 205 is controllably movable along a Z-axis that is generally orthogonal to the X and Y axes, by using a controllable motor 294.

A workpiece 20, or a tray or fixture holding a plurality of workpieces 20, which is to be imaged using the machine vision inspection system 100, is placed on the workpiece stage 210. The workpiece stage 210 may be controlled to move relative to the optical assembly portion 205, such that the interchangeable objective lens 250 moves between locations on a workpiece 20, and/or among a plurality of workpieces 20. One or more of a stage light 220, a coaxial light 230, and a surface light 240 may emit source light 222, 232, or 242, respectively, to illuminate the workpiece(s) 20. The source light is reflected or transmitted as workpiece light 255, which passes through the interchangeable objective lens 250 and the turret lens assembly 280 and is gathered by the camera system 260. The image of the workpiece(s) 20, captured by the camera system 260, is output on a signal line 262 to the control system portion 120. The light sources 220, 230, and 240 may be connected to the control system portion 120 through signal lines or buses 221, 231, and 241, respectively. To alter the image magnification, the control system portion 120 may rotate the turret lens assembly 280 along axis 284 to select a turret lens, through a signal line or bus 281.

In various exemplary embodiments, the optical assembly portion 205 is movable in the vertical Z-axis direction relative to the workpiece stage 210 using a controllable motor 294 that drives an actuator, a connecting cable, or the like, to move the optical assembly portion 205 along the Z-axis to change the focus of the image of the workpiece 20 captured by the camera system 260. The term Z-axis, as used herein, refers to the axis that is intended to be used for focusing the image obtained by the optical assembly portion 205. The controllable motor 294, when used, is connected to the input/output interface 130 via a signal line 296.

As shown in FIG. 2, in various exemplary embodiments, the control system portion 120 includes a controller 125, the input/output interface 130, a memory 140, a workpiece program generator and executor 170, and a power supply portion 190. Each of these components, as well as the additional components described below, may be interconnected by one or more data/control buses and/or application programming interfaces, or by direct connections between the various elements.

In various embodiments according to the present disclosure, the workpiece program generator and executor 170 includes an editing portion 172 that provides or activates various operations and user interface features related to editing a part program, as will be described in greater detail below. It will be appreciated that the terms "workpiece program" and "part program" may be used interchangeably herein. In general, the editing portion 172 includes an editing operations controller 174 that controls the operations for the editing functions, and an editing interface 176 that provides the user interface features for the editing functions. The workpiece program generator and executor 170 also includes a stream mode portion 178, which provides various features associated with the present disclosure, as will be described in more detail below.

As shown in FIG. 2, the input/output interface 130 includes an imaging control interface 131, a motion control interface 132, a lighting control interface 133, and a lens control interface 134. The motion control interface 132 may include a position control element 132a, and a speed/acceleration control element 132b, although such elements may be merged and/or indistinguishable. The lighting control interface 133 includes lighting control elements 133a-133n that control, for example, the selection, power, on/off switch, and strobe pulse timing if applicable, for the various corresponding light sources of the machine vision inspection system 100.

The memory 140 includes an image file memory portion 141, a workpiece program memory portion 142 that may include one or more part programs, or the like, and a video tool portion 143. The video tool portion 143 includes video tool portion 143*a* and other video tool portions (e.g., 143*m*) that determine the GUI, image processing operation, etc., for each of the corresponding video tools. Many known video tools are included in commercially available machine vision inspection systems, such as the QUICK VISION® series of vision systems and the associated QVPAK® software, discussed above. The video tool portion 143 also includes a region of interest (ROI) generator 143*x* that supports automatic, semi-automatic, and/or manual operations that define various ROIs that are operable in various video tools included in the video tool portion 143.

In general, the memory portion 140 stores data usable to operate the vision system components portion 200 to capture or acquire an image of the workpiece 20 such that the acquired image of the workpiece 20 has desired image characteristics. The memory portion 140 may also store inspection result data, may further store data usable to operate the machine vision inspection system 100 to perform various inspection and measurement operations on the acquired images (e.g., implemented, in part, as video tools), either manually or automatically, and to output the results through the input/output interface 130. The memory portion 140 may also contain data defining a user interface operable through the input/output interface 130.

The signal lines or buses 221, 231 and 241 of the stage light 220, the coaxial light 230, and the surface light 240, respectively, are all connected to the input/output interface 130. The signal line 262 from the camera system 260 and the signal line 296 from the controllable motor 294 are connected to the input/output interface 130. In addition to carrying image data, the signal line 262 may carry a signal from the controller 125 that initiates image acquisition.

One or more display devices 136 (e.g., the display 16 of FIG. 1) and one or more input devices 138 (e.g., the joystick 22, keyboard 24, and mouse 26 of FIG. 1) can also be connected to the input/output interface 130. The display devices 136 and input devices 138 can be used to display a user interface that may include various user interface features that are usable to perform inspection operations, and/or to create and/or modify part programs, to view the images captured by the camera system 260, and/or to directly control the vision system components portion 200.

In various exemplary embodiments, when a user utilizes the machine vision inspection system 100 to create a part program for the workpiece 20, the user generates part program instructions either by explicitly coding the instructions automatically, semi-automatically, or manually, using a workpiece programming language, and/or by generating the instructions by operating the machine vision inspection system 100 in a learn mode to provide a desired image acquisition training sequence. For example, a training sequence may comprise positioning a workpiece feature in the field of view (FOV), setting light levels, focusing or autofocusing, acquiring an image, and providing an analysis training sequence applied to the image (e.g., using video tools). The learn mode operates such that the sequence(s) are captured or recorded and converted to corresponding part program steps (i.e., instructions). These part program steps, when the part program is executed, will cause the machine vision inspection system to reproduce the trained image acquisition and analysis operations to automatically inspect a workpiece or workpieces 20 matching the workpiece used when creating the part program.

Related editing features and functions are also described in patent applications entitled "Machine Vision System Program Editing Environment Including Real Time Context Generation Features" (U.S. Pre-Grant Publication No. 2013/0123945); "Machine Vision System Program Editing Environment Including Synchronized User Interface Features" (U.S. Pre-Grant Publication No. 2013/0125044); "System and Method Utilizing An Editing Initialization Block In A Part Program Editing Environment In A Machine Vision System" (U.S. Pre-Grant Publication No. 2013/0120567), each of which is filed concurrently herewith and hereby incorporated by reference.

Figure 3:
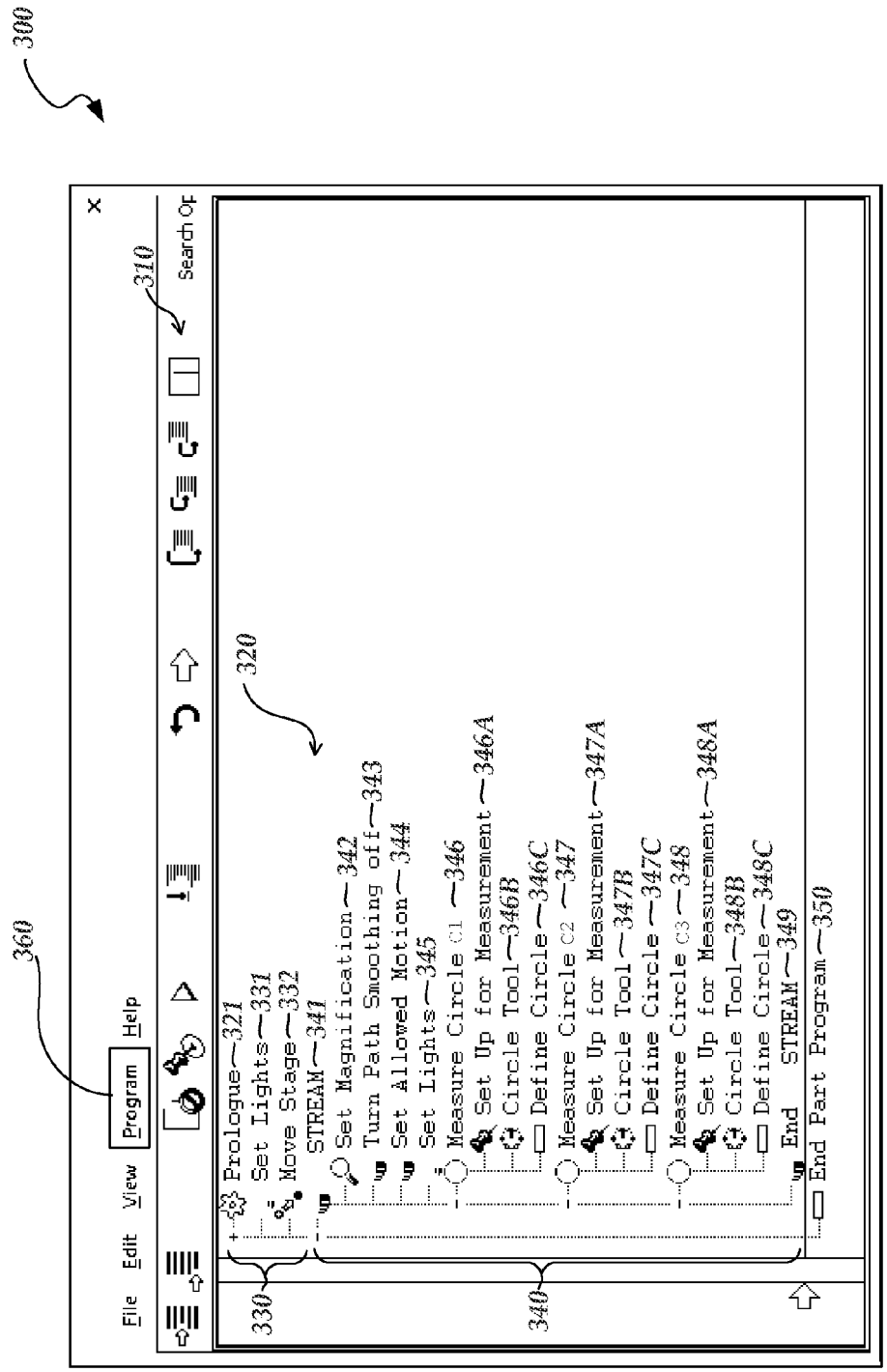
FIG. 3 is a diagram of an editing interface including a representation of a part program that includes a stream mode segment for which a continuous stream of image acquisition operations is performed during a run mode.

FIG. 3 is a diagram of an editing interface 300 including various measurement and/or operation selection bars such as the selection bar 310, and an editable representation of a part program 320 corresponding to various part program instructions that includes a nonstream mode segment representation 330 and a stream mode segment representation 340. The nonstream mode segment representation 330 includes a set of part program instruction representations 331 and 332, and the stream mode segment representation 340 includes a set of part program instruction representations 341-349. The stream mode segment 340 is a segment of the part program 320 that is designated for stream mode execution, as will be described in more detail below. The operation of the specific part program instructions 331-349 will be described in more detail below with respect to FIG. 4.

Figure 4:
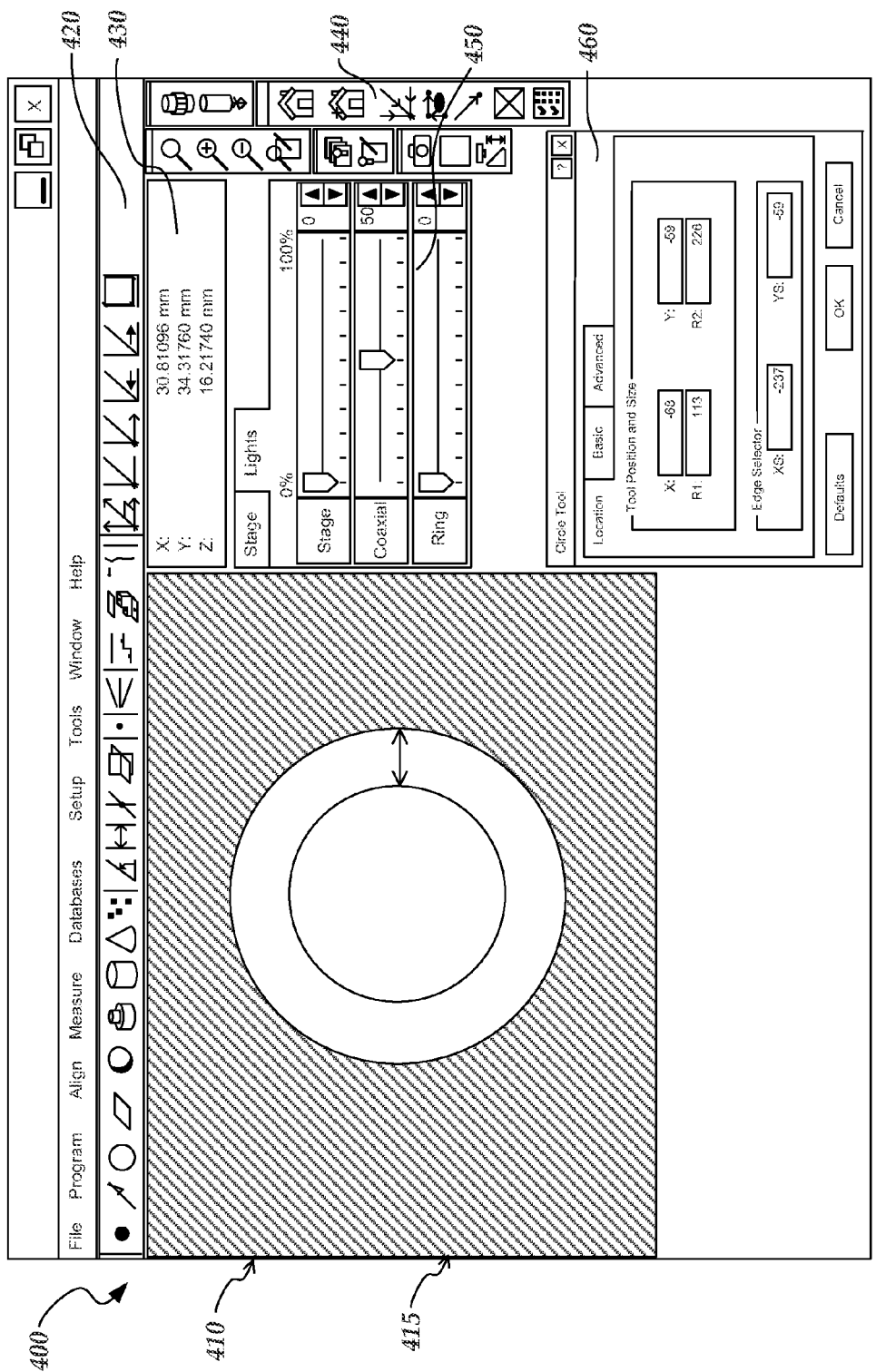
FIG. 4 is a diagram of a user interface including a portion of a workpiece on which the part program steps of FIG. 3 are performed.

FIG. 4 is a diagram illustrating a user interface 400 including a field of view window 410 with a portion of a workpiece 415. The user interface 400 also includes various measurement and/or operation selection bars, such as the selection bars 420 and 440, a real time X-Y-Z (position) coordinate window 430, a light control window 450, and a video tool parameter box 460. As will be described in more detail below, various features on the workpiece 415 are determined in accordance with the related part program instructions of FIG. 3.

The following description will make reference to both the part program instruction representations 321-350 of FIG. 3 and the corresponding actions with regard to the workpiece 415 of FIG. 4. As shown in FIG. 3, the part program 320 begins with the instruction representations 321, 331, and 332 that indicate the prologue node in which the lights are set and the stage is moved to the desired location, respectively. With regard to FIG. 4, the setting of the lights would be visible in terms of the lighting in the field of view window 410, and the movement of the stage would be visible in the field of view window 410 and indicated in the real-time X-Y-Z (position) coordinate window 430. As will be described in more detail below, the instruction representations 331 and 332 are part of the nonstream mode segment representation 330, which in the illustration of FIG. 3 is followed by the stream mode segment representation 340. It will be appreciated that while for purposes of illustration the nonstream mode segment representation 330 has been made to only include two instruction representations, in a more detailed embodiment more instruction representations may be included, such as video tool instruction representations, etc., as will be described in more detail below.

The instruction representation 341 is a stream mode instruction element that designates the start of the stream mode segment 340. The instruction representation 341 may be inserted by activating the stream mode portion 178, for example, through a menu selection under a program menu

360. The instruction representations 342, 343, 344, and 345 then indicate that the magnification is set, the path smoothing is turned off, the allowed motion is set, and the lights are set, respectively.

The instruction representation 346 then indicates that a circle tool will be opened for measuring a circle C1, as indicated by the corresponding instruction representations 346A-346C. More specifically, the instruction representation 346A indicates a set up for measurement (e.g., including the movement of the stage to a designated location and an acquisition of a corresponding image), while the instruction representation 346B indicates the utilization of a circle tool to determine edge points of the circle C1 that is located in the acquired image. The functions and operations of circle tools and other edge detection video tools are known in the art and are described in more detail in the previously incorporated references. As shown in FIG. 4, a circle tool is illustrated in the field of view window 410 as overlaying a circle feature (e.g., such as the circle C1) on the workpiece 415. The edge points that are determined by the circle tool are then utilized by the instruction representation 346C to define the circle C1.

Similarly, the instruction representations 347 and 348 indicate that circle tools will be opened for measuring circles C2 and C3, respectively, as indicated by the corresponding instruction representations 347A-347C and 348A-348C. More specifically, the instruction representations 347A and 348A indicate a set up for measurement (e.g., including the movement of the stage to designated locations and acquisition of corresponding images), while the instruction representations 347B and 348B indicate the utilization of a circle tool to determine edge points of the circles C2 and C3 that are located in the acquired images. With reference to FIG. 4, this indicates that the stage would be moved such that the field of view window 415 would show the movement from the circle feature C1 to the circle features C2 and C3, respectively, for the acquisition of the corresponding images. The edge points that are determined by the circle tools are then utilized by the instruction representations 347C and 348C to define the circles C2 and C3. The instruction representation 349 is a stream mode instruction element that designates the end of the stream mode segment 340. The instruction representation 350 indicates the end of the part program.

With regard to the original creation of the part program 320, part program instructions are recorded during a learn mode in accordance with user input (e.g., as provided through the user interface to control operations of the machine vision inspection system). Thereafter, during an edit mode, the above-described part program instruction representations 321-350 are provided in an editing interface, such as the editing interface 300 of FIG. 3, to represent the corresponding part program instructions (e.g., as written in a programming language) in a simplified form for convenience and ease of use. As will be described in more detail below, while the sequence of part program instruction representations 341-349 in the stream mode segment 340 are represented in the editing mode in a first order (i.e., in the order illustrated in FIG. 3), during a run mode, in accordance with the present disclosure the corresponding part program instructions may be executed according to a second order.

More specifically, in one embodiment, the run mode comprises a stream mode of execution applicable to identified stream segments and the stream mode is configured such that the part program instructions corresponding to the stream mode segment representation 340 are processed to identify the image acquisition operations included in the stream segment (e.g., a plurality of image acquisition operations). The image acquisition process for the plurality of images may begin as soon as this processing allows. Furthermore, the part program instructions corresponding to the stream mode segment representation 340 are processed to identify the image analysis operations corresponding to the acquired images, and the identified image analysis instructions (e.g., video tool operations) may begin as soon as their corresponding images are acquired, provided that this does not interrupt the sequence of image acquisition operations (e.g., a continuous motion used for acquiring the images may continue without dependence on the image analysis operations).

As a specific example, the order of operations of the part program 320 is performed as follows. The instruction representation 321 for the prologue node, as well as the instruction representations 331 and 332 for the setting of the lights and moving of the stage (which are part of the nonstream mode segment representation 330), are performed in the order shown. As described above, once the instruction representation 341 is reached, this indicates the start of the stream mode segment representation 340 that begins the stream mode processing. In the stream mode, the stream mode segment 340 is gone through a first time to determine a list of image acquisition operations, which is then executed, and then a second time to begin execution of image analysis operations (e.g., video tool operations).

More specifically, the first time through the stream mode segment 340, in one embodiment, any operations that are required for acquiring images are added to the list for an image acquisition routine, while any operations that are not required for image acquisition operations are ignored. In one specific example embodiment, the instruction representations 342-345, which are all part of setting up the machine vision inspection system for acquiring the images, are thus added to the list of operations that will be part of the image acquisition routine. In contrast, the part program instruction representation 346, which indicates that a circle measurement tool will need to be opened, is not added to the list for the image acquisition routine because it is not required for acquiring the corresponding image. However, the instruction representation 346A, which indicates a setup for measurement, which includes going to a position and collecting an image, is added to the list for the image acquisition routine. The instruction representations 346B and 346C, which relate to running the circle tool and defining the circle, are not required for image acquisition and thus are ignored rather than being added to the list. In a similar manner, the instruction representation 347 is ignored, the instruction representation 347A is added to the list, the instruction representations 347B, 347C, and 348 are ignored, the instruction representation 348A is added to the list, and the instruction representations 348B and 348C are ignored.

After the first time through the stream mode segment 340, once the image acquisition routine has been determined according to the instruction representations 342-345, 346A, 347A, and 348A, the execution of the image acquisition routine is begun. While the image acquisition routine is being executed, the stream mode segment 340 is gone through a second time, during which the image analysis operations (e.g., video tool operations) are executed. During the second time through, in one embodiment, the instruction representations 342-345, which do not include any image analysis operations, are ignored. The instruction representation 346, which indicates that a circle measurement will need to be opened, is executed.

The instruction representation 346A is a special case, which indicates both image acquisition and image analysis operations, as will be described in more detail below. Briefly, during the second time through, the instruction representation 346A, which previously indicated image acquisition operations, also indicates that an image needs to be loaded, which is an image analysis operation, and so is executed. More specifically, if the image indicated by the instruction representation 346A has already been acquired by the image acquisition routine that was started as indicated above, then the image is loaded. If the image has not yet been acquired, then the process for the second time through is temporarily halted until the image is acquired by the image acquisition routine. Thus, as illustrated by the instruction representation 346A, certain instruction representations may indicate operations that are executed during both the first and second times through the stream mode segment 340.

After the execution of the instruction representation 346A, the second time through continues with the instruction representations 346B and 346C that are executed for running the circle tool and defining the circle C1 according to the edge points determined by the circle tool. Similarly, the instruction representation 347 is executed, and the instruction representation 347A for loading the corresponding image of the circle C2 is executed if the image has been acquired by the image acquisition routine, and waited for if the image has not yet been acquired. After the execution of the instruction representation 347A, the instruction representations 347B, 347C, and 348 are executed, with the instruction representation 348A being executed if the corresponding image is available or otherwise waited for if the image has not yet been acquired. After the execution of the instruction representation 348A, the instruction representations 348B and 348C are executed, with the instruction representation 349 indicating the end of the stream mode segment 340 and the end of the stream mode. It will be appreciated that in an embodiment where additional instruction representations followed the stream mode segment 340, these would be outside of the stream mode and would be executed in the order shown according to the nonstream mode, similar to the instruction elements 331 and 332 of the nonstream mode segment 330.

It will be appreciated that the above-described operations and editing environment for a stream mode segment are advantageous over certain prior art implementations. More specifically, in certain previous implementations, an explicit list of commands were utilized for image acquisition, and a different explicit list of commands were utilized for analyzing the images that were acquired. In order to achieve continuous-motion type image acquisitions, at the time of programming, the image acquisition instructions were organized into a separate list, and were in different programming representations and syntax in the part program. This made editing and "debugging" of the corresponding part programs more difficult. More specifically, when a user returned to a part program where the operations had been reordered and different programming representations and syntax had been used for continuous-motion type image acquisition, it was more confusing to determine how to edit or reprogram instructions that were inside of the continuous-motion image acquisition routine as opposed to outside. In addition, debugging of the part program was further complicated, in that there was no easily viewable representation of the steps as they had originally been performed, which thus made it more difficult to determine which instructions had caused which results.

In accordance with the present disclosure, as described above, a more desirable editing environment is provided in which the part program instruction representations may be provided in their original order. Furthermore, instruction representations inside of a stream mode segment (e.g., stream mode segment 340) are made to have an identical appearance to those outside of a stream mode segment. As a specific example, if the instruction representations 346, 346A, 346B, and 346C had been recorded outside of the stream mode segment 340 (e.g., within the nonstream mode segment 330), they would have an identical appearance in the editing interface 300 aside from the representation of being "contained" by the instruction representation 341. This is in contrast to the prior art methods described above, wherein such instruction representations would be provided in a different programming representation and syntax inside of a stream mode segment as compared to outside. As described above, the representation of the part program 320 as illustrated in the editing interface 300 also allows debugging of the part program to be performed in a sequential manner even within the stream mode segment 340. More specifically, during a debugging process (e.g., during the editing mode), a user may elect to have the instruction representations within the stream mode segment 340 executed in the first order (i.e., the order indicated in the editing representation 300) that is the order in which they were originally programmed, in a step-by-step process, in order to simplify the determination of which instruction representations are causing which results.

Figure 5A:
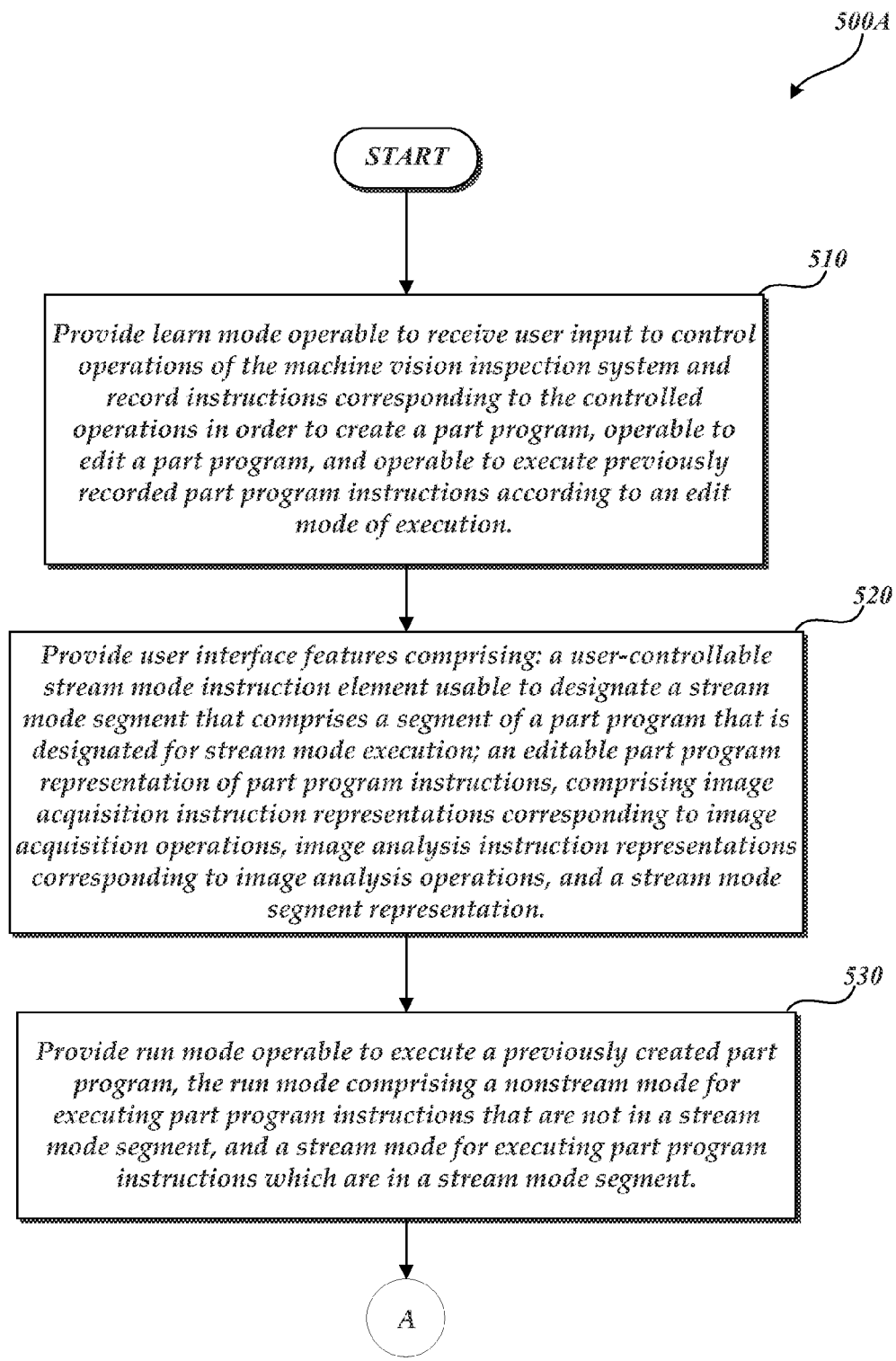
FIGS. 5A and 5B are flow diagrams of one embodiment of a routine for providing an editing environment for a part program including a stream mode segment.
Figure 5B:
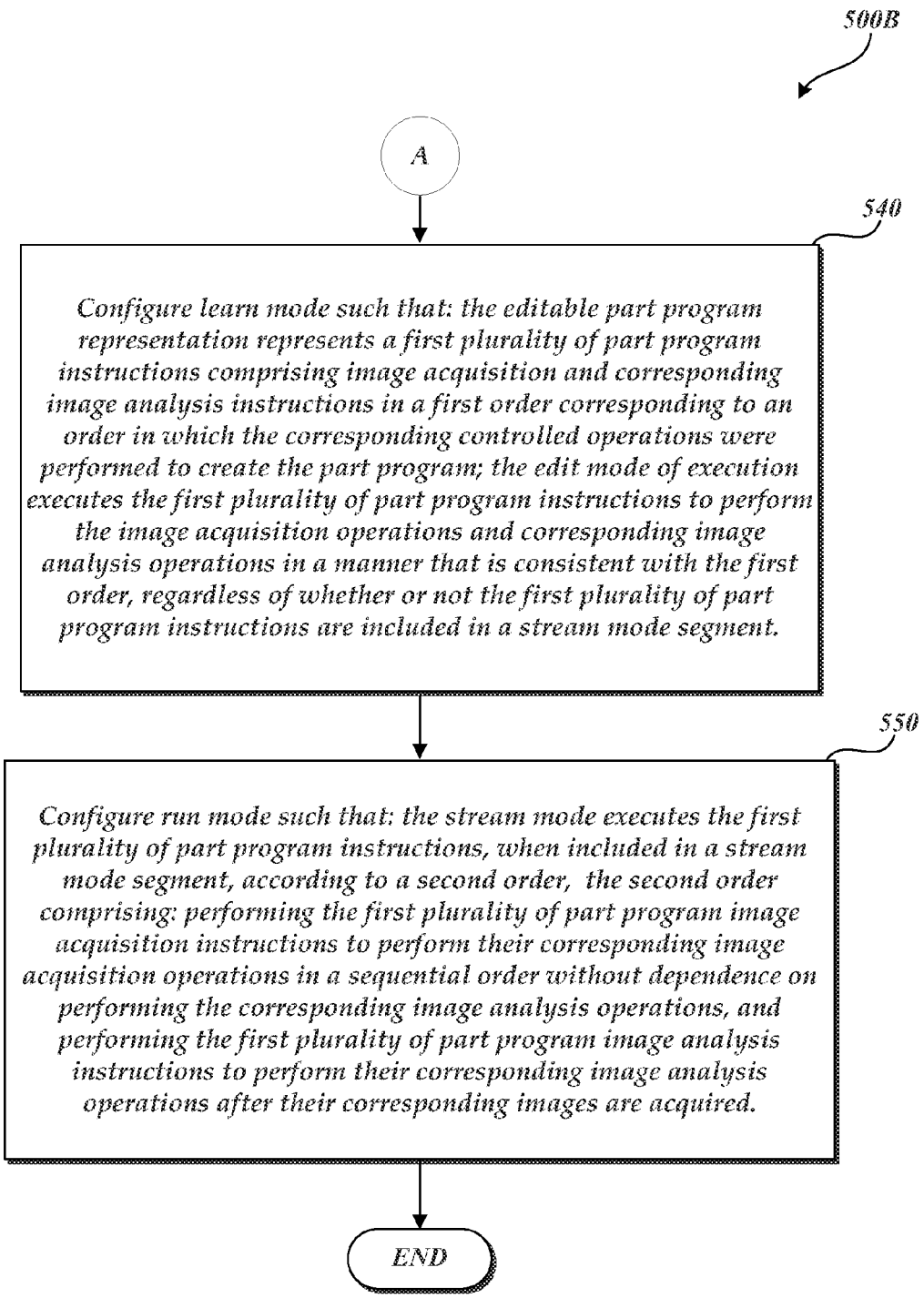

FIGS. 5A AND 5B are flow diagrams 500A and 500B of one embodiment of a routine for providing an editing environment for a part program including a stream mode segment. As shown in FIG. 5A, at a block 510, a learn mode is provided that is operable to receive user input to control operations of the machine vision inspection system and record instructions corresponding to the controlled operations in order to create a part program. The learn mode is also operable to edit a part program and to execute previously recorded part program instructions according to an edit mode of execution.

At a block 520, user interface features are provided including a user-controllable stream mode instruction element and an editable part program representation of part program instructions. The user-controllable stream mode instruction element is usable to designate a stream mode segment that comprises a segment of a part program that is designated for stream mode execution. The editable part program representation may include image acquisition instruction representations corresponding to image acquisition operations, image analysis instruction representations corresponding to image analysis operations, and a stream mode segment representation.

At a block 530, a run mode is provided that is operable to execute a previously created part program, the run mode comprising a nonstream mode for executing part program instructions that are not in a stream mode segment, and a stream mode for executing part program instructions that are in a stream mode segment. From the block 530, the routine continues to a point A, as will be described in more detail below with respect to FIG. 5B.

As shown in FIG. 5B, from the point A, the routine continues to a block 540. At the block 540, the learn mode is configured such that the editable part program representation represents a first plurality of part program instructions comprising image acquisition and corresponding image analysis instructions in a first order corresponding to an order in which the corresponding controlled operations were performed to create the part program. The learn mode is further configured such that the edit mode of execution executes the part program instructions to perform the image acquisition operations and corresponding image analysis operations in a manner that is consistent with the first order, regardless of whether or not the first plurality of part program instructions are included in a stream mode segment.

At a block 550, the run mode is configured such that the stream mode executes the first plurality of part program instructions, when included in a stream mode segment, according to a second order. The second order includes performing the first plurality of part program image acquisition instructions to perform their corresponding image acquisition operations in a sequential order without dependence on performing the corresponding image analysis operations. In one embodiment, the image acquisition operations may be performed in the sequential order during a continuous motion sequence. The second order further includes performing the first plurality of part program image analysis instructions to perform their corresponding image analysis operations after their corresponding images are acquired.

Although the previous description has emphasized embodiments that include explicit stream mode segment marking or indication, stream mode segment marking and/or recognition of a separate mode or stream of operations may be incomprehensible or irrelevant to some users. For example, stream mode execution may be available on all machines possessed by a user and/or may be the default or only mode of execution used for run mode execution on a machine, so there may be no need to distinguish stream mode operation(s) for special recognition or consideration. Therefore, stream mode user interface representations and code markings such as the part program representation 341 may be eliminated in some embodiments; for example, in various embodiments similar to those described below with reference to FIGS. 6, 7A, and 7B. For example, in some embodiments, some or all stream mode compatible instructions and/or operations may be automatically executed in stream mode during run mode. In some implementations, this may be the default or only setting for run mode execution. In other implementations, the user may select either stream or nonstream mode execution as the global "automatic" mode of execution during run mode.

In any case, it should be appreciated that regardless of whether stream mode instructions are explicitly marked in a user interface or defined in a part program to indicate stream mode execution during run mode, many or all of the previously described features and benefits of nonstream edit mode representation and execution remain desirable and advantageous for users during learn mode and/or editing operations, for previously outlined reasons.

To generally summarize such an embodiment, a precision machine vision inspection system may comprise an imaging portion, a stage for holding one or more workpieces in a field of view (FOV) of the imaging portion, a control portion, a display, and a user interface. The machine vision inspection system may further comprise a learn mode operable to receive user input to control operations of the machine vision inspection system and record instructions corresponding to the controlled operations in order to create a part program, operable to edit a part program, and operable to execute previously recorded part program instructions according to an edit mode of execution. The learn mode may include user interface features comprising an editable part program representation of part program instructions, comprising image acquisition instruction representations corresponding to image acquisition operations and image analysis instruction representations corresponding to image analysis operations. The machine vision inspection system may further comprise a run mode operable to execute a previously created part program, the run mode comprising a stream mode for executing part program instructions. The learn mode may be configured such that the editable part program representation represents a first plurality of part program instructions comprising image acquisition and corresponding image analysis instructions in a first order corresponding to an order in which the corresponding controlled operations were performed to create the part program, and the edit mode of execution executes the part program image acquisition instructions and corresponding image analysis instructions of the first plurality of part program instructions to perform the image acquisition operations and corresponding image analysis operations in a manner that is consistent with the first order. The run mode may be configured such that the stream mode executes the first plurality of part program instructions according to a second order, the second order comprising performing the first plurality of part program image acquisition instructions to perform their corresponding image acquisition operations in a sequential order without dependence on performing the corresponding image analysis operations, and performing the first plurality of part program image analysis instructions to perform their corresponding image analysis operations after their corresponding images are acquired.

Figure 6A:
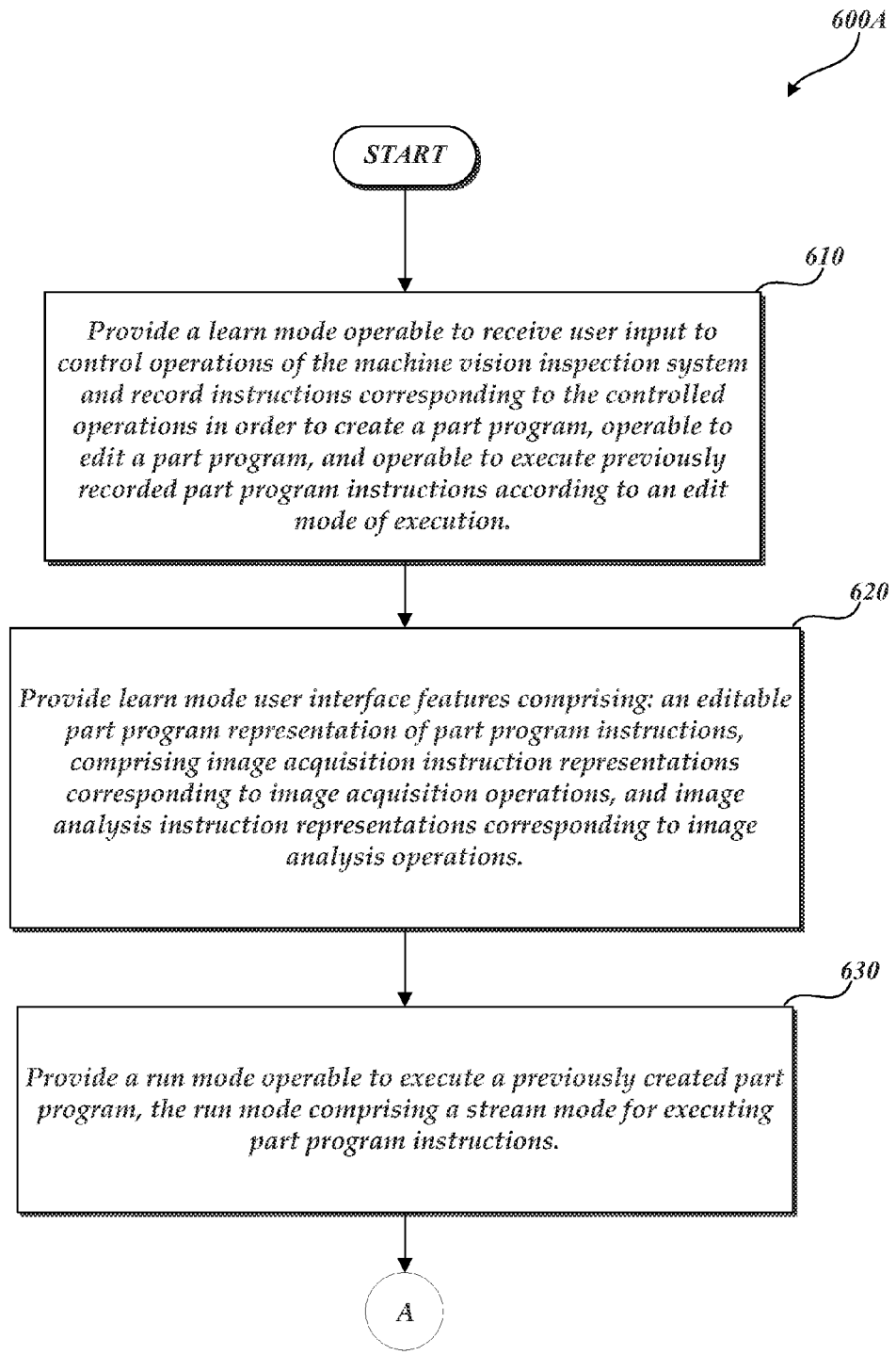
FIGS. 6A and 6B are flow diagrams of one embodiment of a routine for implementing an embodiment wherein a part program may be executed using a stream mode of operations during run mode, while a "nonstream" edit mode of representation and execution may be used during learn mode.
Figure 6B:
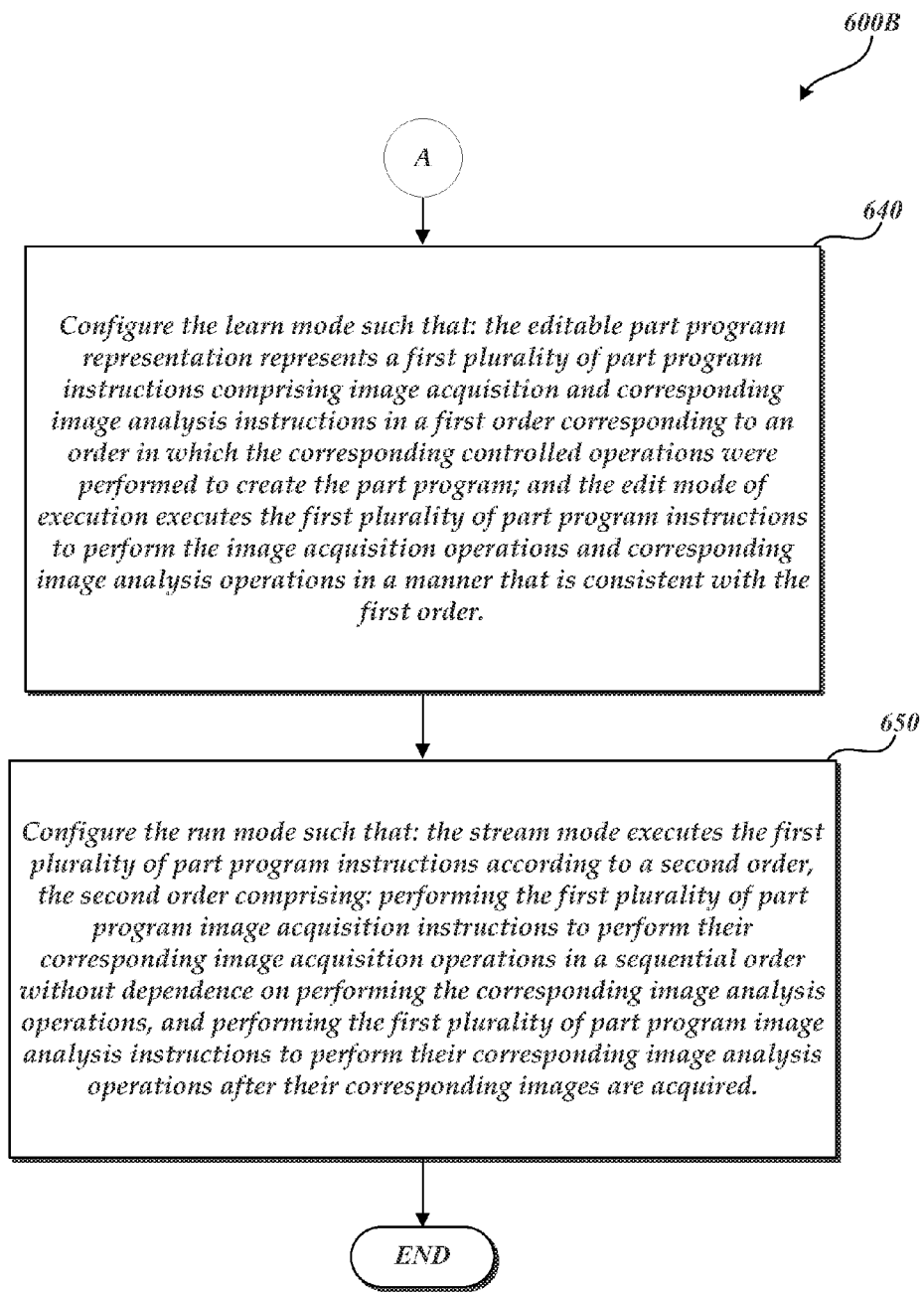

FIGS. 6A and 6B are flow diagrams 600A and 600B of one embodiment of a routine for implementing an embodiment consistent with that outlined immediately above, wherein a part program may generally be executed using a stream mode of operations during run mode, while a more user-friendly "nonstream" edit mode of representation and execution may be used during learn mode.

As shown in FIG. 6A, at a block 610, a learn mode is provided that is operable to receive user input to control operations of the machine vision inspection system and record instructions corresponding to the controlled operations in order to create a part program. The learn mode is also operable to edit a part program and to execute previously recorded part program instructions according to an edit mode of execution. At a block 620, user interface features are provided including an editable part program representation of part program instructions. The editable part program representation may include image acquisition instruction representations corresponding to image acquisition operations and image analysis instruction representations corresponding to image analysis operations. At a block 630, a run mode is provided that is operable to execute a previously created part program, the run mode comprising a stream mode for executing part program instructions. From the block 630, the routine continues to a point A, as will be described in more detail below with respect to FIG. 6B.

As shown in FIG. 6B, from the point A, the routine continues to a block 640. At the block 640, the learn mode is configured such that the editable part program representation represents a first plurality of part program instructions comprising image acquisition and corresponding image analysis instructions in a first order corresponding to an order in which the corresponding controlled operations were performed to create the part program. The learn mode is further configured such that the edit mode of execution executes the part program instructions to perform the image acquisition operations and corresponding image analysis operations in a manner that is consistent with the first order. At a block 650, the run mode is configured such that the stream mode executes the first plurality of part program instructions according to a second order. The second order includes performing the first plurality of part program image acquisition instructions to perform their corresponding image acquisition operations in a sequential order without dependence on performing the corresponding image analysis operations. In one embodiment, the image acquisition operations may be performed in the sequential order during a continuous motion sequence. The second order may further include performing the first plurality of part program image analysis instructions to perform their corresponding image analysis operations after their corresponding images are acquired.

In one embodiment, performing the first plurality of part program image acquisition instructions to perform their corresponding image acquisition operations in a sequential order may comprise performing image acquisition operations during a continuous image acquisition sequence wherein the stage and the imaging portion move approximately continuously relative to one another for acquiring the images except for image acquisition motion operations required to limit image blur at imaging locations, and without motion delays due to image analysis operations. For example, with respect to the part program 320 shown in FIG. 3, during the operations corresponding to the instruction representation 346A, a set up for measurement may include movement of the stage to a designated location and an acquisition of a corresponding image while the movement is either stopped or slowed down sufficiently to limit image blur. Similar movement may be utilized for the operations corresponding to the instruction representations 347A and 348A.

The previous description has emphasized embodiments wherein the machine vision inspection system includes strobe illumination or other means to allow fast image exposure without blur during stream mode execution of a part program. In such systems, the performance of the image acquisition operations in a sequential order may be done during a truly continuous motion sequence wherein the stage and the imaging portion move continuously relative to one another without stopping. However, in other embodiments wherein the machine vision inspection system lacks strobe illumination or otherwise requires slowing or momentarily stopping the relative motion to limit image blur, the performance of the image acquisition operations in the sequential order during stream mode execution may be done while using an approximately continuous motion sequence and the significant benefits outlined previously may still be retained. In various embodiments, the approximately continuous motion sequence may then include the necessary motion operations that prevent image blur (e.g., slowing or momentarily stopping the otherwise continuous motion as dictated by image acquisition requirements), but does not include motion delays related to performing image analysis, or the like, in order to reduce or minimize the overall execution time of the part program during stream mode execution. This idea is clarified with reference to FIG. 7.

Figure 7:
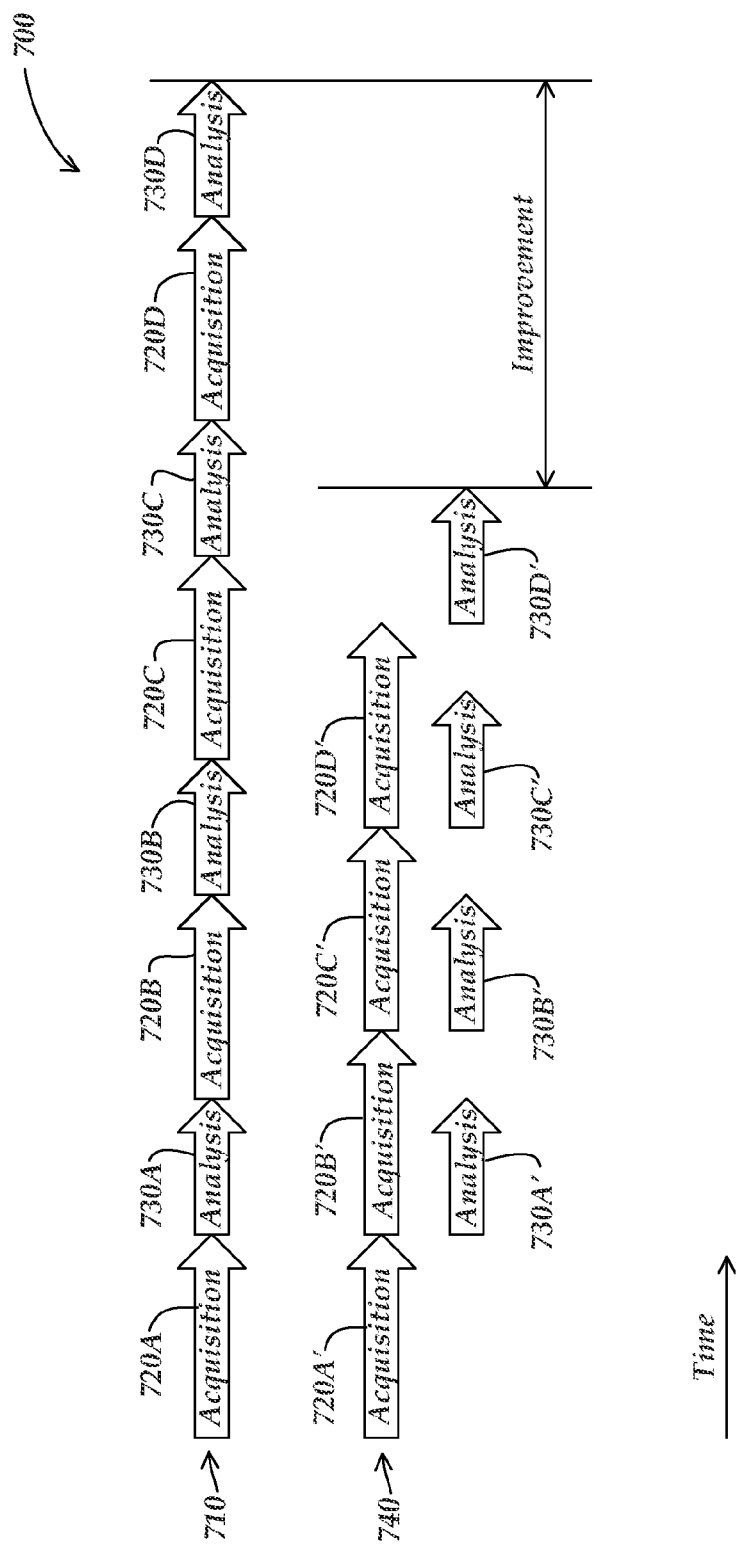
FIG. 7 is a timing diagram 700 that characterizes one aspect of a nonstream or edit mode of execution in comparison to a stream mode of execution.

FIG. 7 is a timing diagram 700 that characterizes one aspect of one exemplary embodiment of a nonstream or edit mode of execution 710 and one exemplary embodiment of stream mode execution 740. The timing sequence associated with the nonstream or edit mode of execution 710 does not indicate a sequential image acquisition sequence. Rather, first, an image acquisition operation 720A is performed, which may include operations wherein a stage and the imaging portion move relative to one another in order to place a feature in a field of view of the imaging system, image illumination is provided, and so on as needed to acquire an image. After the image acquisition operation 720A, an image analysis operation 730A is performed on that acquired image that may include operations such as edge detection based on an image acquired during the image acquisition operation 720A. After the image analysis operation 730A is complete, an image acquisition operation 720B is performed (e.g., analogous to the operation 720A), and after completion, an image analysis operation 730B is performed. This pattern continues with image acquisition operations 720C and 720D and image analysis operations 730C and 730D, and so on. Each image analysis operation may interrupt and delay the subsequent image acquisition. Such an execution is advantageous and easily understood during learn mode, when user actions are required to define the image acquisition parameters, and the image analysis results need to be evaluated to confirm that a desirable image has yielded the expected analysis results prior to moving on to defining or verifying the next part program operation. In such a case, the image analysis time does not significantly delay the overall learn mode process that is typically paced by user input and evaluation, and the like.

In contrast, the timing sequence associated with the stream mode of execution 740 indicates a sequential image acquisition sequence. First, an image acquisition operation 720A' is performed that may be similar to the image acquisition operation 720A in this example and include operations wherein a stage and the imaging portion move relative to one another in order to place a feature in a field of view of the imaging system, image illumination is provided, and so on as needed to acquire an image. After the image acquisition operation 720A' is complete, the image acquisition operation 720B' is immediately initiated and performed, since the motion between image acquisition locations is typically one of the more time consuming in an inspection sequence, and governs the overall throughput. Subsequent image acquisition operations 720C', 720D', and so on, follow a similar pattern for that reason, forming a sequential image acquisition sequence. In modern computers, the image analysis operations corresponding to any particular image may be initiated at any practical time after that image is acquired and/or stored in memory. In this example, the image analysis operation 730A', which may include operations (e.g., similar or identical to the image analysis operations 730A) such as edge detection analysis for an edge included in the image of operation 720A', is initiated immediately after the image acquisition operation 720A' is completed, and is performed in parallel with the image acquisition operation 720B'. Subsequent image analysis operations 730B', 730C', 730D', and so on, follow a similar pattern. The result is an improvement in the time that the stream mode of execution 740 takes to perform the same number of image acquisition and analysis operations compared to the nonstream or edit mode of execution 710.

In embodiments where the machine vision inspection system includes strobe illumination or other means to allow fast image exposure without blur, the performance of the image acquisition operations in a sequential order during the stream mode 740 is done during a truly continuous motion sequence wherein the stage and the imaging portion move continuously relative to one another. This is the ideal case, and will typically result in the shortest execution times. In embodiments wherein the machine vision inspection system lacks strobe illumination, or otherwise requires slowing or momentarily stopping the relative motion to limit image blur, the performance of the image acquisition operations in the sequential order during the stream mode 740 may be done during an "approximately continuous" motion sequence. The approximately continuous motion sequence may include motion operations that prevent image blur (e.g., slowing or momentarily stopping the otherwise continuous motion as dictated by image acquisition requirements), but does not include motion delays related to performing image analysis, or the like. Stream mode execution in such an embodiment is still advantageous. Experimental results show that one exemplary part program on a nonstream or "conventional" machine vision inspection system which collects 16 images in a 4×4 array with 1 mm steps in the X-Y plane executes approximately 40% faster using the stream mode 740 than it does using the nonstream or edit mode of execution 710, even when momentarily stopping or substantially slowing during performance of image acquisition operations in a sequential order during an approximately continuous image acquisition sequence. Thus, generally, various embodiments outlined herein may comprise performing image acquisition operations during a continuous image acquisition sequence comprising at least one of (a) operations wherein the stage and the imaging portion move continuously relative to one another for acquiring the images, or (b) operations wherein the stage and the imaging portion move approximately continuously relative to one another for acquiring the images except for image acquisition motion operations required to limit image blur at imaging locations, and without motion delays due to image analysis operations.

While various preferred and exemplary embodiments of the present disclosure have been illustrated and described, it will be appreciated that various changes can be made therein without departing from the spirit and scope of the present disclosure.

The embodiments of the invention in which an exclusive property or privilege is claimed are defined as follows:

1. A precision machine vision inspection system comprising an imaging portion, a stage for holding one or more workpieces in a field of view (FOV) of the imaging portion, a control portion including a processor, a display, and a user interface, wherein the machine vision inspection system further comprises:
a learn mode operable to receive user input to control operations of the machine vision inspection system and record instructions corresponding to the controlled operations in order to create a part program, operable to edit a part program, and operable to execute previously recorded part program instructions according to an edit mode of execution, the learn mode including user interface features comprising:
a user-controllable stream mode instruction element usable to designate a stream mode segment that comprises a segment of a part program that is designated for stream mode execution; and
an editable part program representation of part program instructions, comprising image acquisition instruction representations corresponding to image acquisition operations, image analysis instruction representations corresponding to image analysis operations, and a stream mode segment representation; and
a run mode operable to execute a previously created part program, the run mode comprising a nonstream mode for executing part program instructions that are not in a stream mode segment, and a stream mode for executing part program instructions that are in a stream mode segment, wherein
the learn mode is configured such that:
the editable part program representation represents a first plurality of part program instructions comprising image acquisition and corresponding image analysis instructions in a first order corresponding to an order in which the corresponding controlled operations were performed to create the part program; and
the edit mode of execution executes the part program image acquisition instructions and corresponding image analysis instructions of the first plurality of part program instructions to perform the image acquisition operations and corresponding image analysis operations in a manner that is consistent with the first order, regardless of whether or not the first plurality of part program instructions are included in a stream mode segment; and
the run mode is configured such that:
the stream mode executes the first plurality of part program instructions when included in a stream mode segment, according to a second order, the second order comprising:
performing the first plurality of part program image acquisition instructions to perform their corresponding image acquisition operations in a sequential order during a continuous image acquisition sequence wherein the stage and the imaging portion move approximately continuously relative to one another for acquiring the images except for image acquisition motion operations required to limit image blur at imaging locations without dependence on performing the corresponding image analysis operations, and performing the first plurality of part program image analysis instructions to perform their corresponding image analysis operations after their corresponding images are acquired.

2. The system of claim 1, wherein the performance of the image acquisition operations in a sequential order is done during a continuous motion sequence wherein the stage and the imaging portion move continuously relative to one another for acquiring the images.

3. The system of claim 1, wherein the performance of the image analysis operations after their corresponding images are acquired is performed as least partly during the sequential order of image acquisition operations.

4. The system of claim 1, wherein the nonstream mode of execution executes the image acquisition instructions and corresponding image analysis instructions of the first plurality of part program instructions that are not in a stream mode segment to perform the image acquisition operations and corresponding image analysis operations in a manner that is consistent with the first order.

5. The system of claim 1, wherein the learn mode is configured such that when a part program including a stream mode segment is recalled for editing, the editable part program representation is displayed in the first order, and the edit mode of execution executes the image acquisition operations and corresponding image analysis operations in a manner that is consistent with the first order.

6. The system of claim 1, wherein the learn mode is configured such that a user may select a part program instruction representation included in a stream mode segment as a place to initiate edit mode of execution of corresponding part program instructions, after which the subsequent part program instructions are executed in a manner that is consistent with the first order.

7. The system of claim 6, wherein the subsequent part program instructions are executed in a manner that is consistent with the first order.

8. The system of claim 1, wherein the stream mode segment comprises a first set of instructions and a second set of instructions, the first set of instructions comprising first image acquisition instructions and first image analysis instructions that comprise video tool instructions of a first video tool, and the second set of instructions comprising second image acquisition instructions and second image analysis instructions that comprise video tool instructions of a second video tool, wherein during the edit mode of execution the first image acquisition instructions and first image analysis instructions that comprise video tool instructions of the first video tool are executed before beginning execution of the second image acquisition instructions and the second image analysis instructions which comprise video tool instructions of the second video tool; and during the run mode, the stream mode segment is executed in the stream mode due to the stream mode instruction element, and during the run mode of execution of the stream mode segment, the first and second image acquisition instructions are executed in a sequential order without dependence on performing the corresponding first and second image analysis operations that comprise video tool instructions of the first and second video tool.

9. The system of claim 8, wherein the part program further comprises a nonstream mode segment, and during the learn mode the nonstream mode segment is differentiated from the stream mode segment by the lack of a stream mode instruction element for the nonstream mode segment, the nonstream mode segment comprising a third set of instructions and a fourth set of instructions, the third set of instructions comprising third image acquisition instructions and third image analysis instructions that comprise video tool instructions of a third video tool, and the fourth set of instructions comprising fourth image acquisition instructions and fourth image analysis instructions that comprise video tool instructions of a fourth video tool, wherein during the edit mode of execution the third image acquisition instructions and third image analysis instructions that comprise video tool instructions of the third video tool are executed before beginning execution of the fourth image acquisition instructions and the fourth image analysis instructions that comprise video tool instructions of the fourth video tool; and during the run mode, the nonstream mode segment is executed in the nonstream mode due to the lack of a stream mode instruction element for the nonstream mode segment, and during the run mode execution of the nonstream mode segment, the third and fourth image acquisition instructions are executed in a sequential order without dependence on performing the corresponding third and fourth image analysis operations that comprise video tool instructions of the third and fourth video tool.

10. The system of claim 8, wherein the first and second video tools comprise edge detection video tools.

11. The system of claim 8, wherein during the learn mode the first and second sets of instructions are executed in the first order, wherein at least some of the first and second image acquisition instructions are interspersed with the video tool instructions of the first video tool and the second video tool, the instructions being displayed on the user interface in the first order; and during the run mode, in the stream mode, the part program instruction corresponding to the stream mode segment is processed to determine an image acquisition routine that comprises the image acquisition instructions of the first and second sets of instructions but not the video tool instructions, the image acquisition routine is executed for acquiring the images, and while the image acquisition routine is being executed, the video tool instructions are executed.

12. The system of claim 11, wherein during the run mode, in the stream mode, at least a portion of the execution of the video tool instructions during the second time through the stream mode segment is done in parallel with the execution of the image acquisition routine.

13. The system of claim 11, wherein during the run mode, during the execution of the image acquisition routine, a plurality of the image acquisition instructions are executed in series during which time any video tool instructions that were interspersed during the learn mode are not yet executed, such that the instructions are executed in the second order that is different from the first order.

14. The system of claim 11, wherein during the run mode, when the image acquisition routine is executed, the stage and the imaging portion move continuously relative to one another for acquiring the images.

15. The system of claim 1, wherein the stream mode segment of the part program is identified by stream mode instruction representations at the beginning and end of the stream mode segment.

16. The system of claim 1, wherein during the learn mode, the part program instructions within the stream mode segment that are displayed in a part program representation are made to have an identical appearance to similar part program instructions that are outside of the stream mode segment, such that a user is not required to use a different programming representation or syntax when programming or editing operations that are inside of the stream mode segment as opposed to outside of the stream mode segment.

17. A method for operating a precision machine vision inspection system comprising an imaging portion, a stage for holding one or more workpieces in a field of view (FOV) of the imaging portion, a control portion including a processor, a display, and a user interface, the method comprising:

providing a learn mode operable to receive user input to control operations of the machine vision inspection system and record instructions corresponding to the controlled operations in order to create a part program, operable to edit a part program, and operable to execute previously recorded part program instructions according to an edit mode of execution, the learn mode including user interface features comprising:
a user-controllable stream mode instruction element usable to designate a stream mode segment that comprises a segment of a part program that is designated for stream mode execution; and
an editable part program representation of part program instructions, comprising image acquisition instruction representations corresponding to image acquisition operations, image analysis instruction representations corresponding to image analysis operations, and a stream mode segment representation;

providing a run mode operable to execute a previously created part program, the run mode comprising a nonstream mode for executing part program instructions that are not in a stream mode segment, and a stream mode for executing part program instructions that are in a stream mode segment, wherein the learn mode is configured such that:
the editable part program representation represents a first plurality of part program image acquisition and corresponding image analysis instructions in a first order corresponding to an order in which the corresponding controlled operations were performed to create the part program; and
the edit mode of execution executes the part program image acquisition instructions and corresponding image analysis instructions of the first plurality of part program instructions to perform the image acquisition operations and corresponding image analysis operations in a manner that is consistent with the first order, regardless of whether or not the first plurality of part program image instructions are included in a stream mode segment; and the run mode is configured such that:
    the stream mode executes the first plurality of part program instructions when included in a stream mode segment, according to a second order, the second order comprising:
        performing the first plurality of part program image acquisition instructions to perform their corresponding image acquisition operations in a sequential order including performing image acquisition operations during a continuous image acquisition sequence comprising at least one of (a) operations wherein the stage and the imaging portion move continuously relative to one another for acquiring the images, or (b) operations wherein the stage and the imaging portion move approximately continuously relative to one another for acquiring the images except for image acquisition motion operations required to limit image blur at imaging locations without dependence on performing the corresponding image analysis operations, and performing the first plurality of part program image analysis instructions to perform their corresponding image analysis operations after their corresponding images are acquired.

18. The method of claim 17, wherein when a part program including a stream mode segment is recalled for editing, the editable part program representation is displayed in the first order, and edit mode of execution executes the image acquisition operations and corresponding image analysis operations in a manner that is consistent with the first order.

19. A precision machine vision inspection system comprising an imaging portion, a stage for holding one or more workpieces in a field of view (FOV) of the imaging portion, a control portion, a display, and a user interface, wherein the machine vision inspection system further comprises:
    a learn mode operable to receive user input to control operations of the machine vision inspection system and record instructions corresponding to the controlled operations in order to create a part program, operable to edit a part program, and operable to execute previously recorded part program instructions according to an edit mode of execution, the learn mode including user interface features comprising:
        an editable part program representation of part program instructions, comprising image acquisition instruction representations corresponding to image acquisition operations and image analysis instruction representations corresponding to image analysis operations;
    a run mode operable to execute a previously created part program, the run mode comprising a stream mode for executing part program instructions, wherein
    the learn mode is configured such that:
        the editable part program representation represents a first plurality of part program instructions comprising image acquisition and corresponding image analysis instructions in a first order corresponding to an order in which the corresponding controlled operations were performed to create the part program; and
        the edit mode of execution executes the part program image acquisition instructions and corresponding image analysis instructions of the first plurality of part program instructions to perform the image acquisition operations and corresponding image analysis operations in a manner that is consistent with the first order; and
    the run mode is configured such that:
        the stream mode executes the first plurality of part program instructions according to a second order, the second order comprising:
            performing the first plurality of part program image acquisition instructions to perform their corresponding image acquisition operations in a sequential order without dependence on performing the corresponding image analysis operations, and performing the first plurality of part program image analysis instructions to perform their corresponding image analysis operations after their corresponding images are acquired.

20. The system of claim 19, wherein the performance of the image acquisition operations in a sequential order is done during a continuous image acquisition sequence comprising at least one of (a) operations wherein the stage and the imaging portion move continuously relative to one another for acquiring the images, or (b) operations wherein the stage and the imaging portion move approximately continuously relative to one another for acquiring the images except for image acquisition motion operations required to limit image blur at imaging locations, and without motion delays due to image analysis operations.

21. The system of claim 19, wherein the performance of the image analysis operations after their corresponding images are acquired is performed as least partly during the sequential order of image acquisition operations.

22. The system of claim 19, wherein the learn mode is configured such that when a part program that is executed using the stream mode during run mode is recalled for editing, the editable part program representation is displayed in the first order, and the edit mode of execution executes the image acquisition operations and corresponding image analysis operations in a manner that is consistent with the first order.

23. The system of claim 19, wherein the part program that is executed using the stream mode during run mode comprises a first set of instructions and a second set of instructions, the first set of instructions comprising first image acquisition instructions and first image analysis instructions that comprise video tool instructions of a first video tool, and the second set of instructions comprising second image acquisition instructions and second image analysis instructions that comprise video tool instructions of a second video tool, wherein during the edit mode of execution, the first image acquisition instructions and first image analysis instructions that comprise video tool instructions of the first video tool are executed before beginning execution of the second image acquisition instructions and the second image analysis instructions that comprise video tool instructions of the second video tool; and
    during the run mode, the part program is executed in the stream mode wherein the first and second image acquisition instructions are executed in a sequential order without dependence on performing the corresponding first and second image analysis operations that comprise video tool instructions of the first and second video tool.

24. The system of claim 23, wherein during the learn mode, the first and second sets of instructions are executed in the first order wherein at least some of the first and second image acquisition instructions are interspersed with the video tool instructions of the first video tool and the second video tool, the instructions being displayed on the user interface in the first order; and
    during the run mode, the part program instructions are processed to determine an image acquisition sequence or routine that comprises the image acquisition instructions of the first and second sets of instructions but not the video tool instructions, the image acquisition sequence or routine is executed for acquiring the images, and while the image acquisition sequence or routine is being executed, the video tool instructions are executed.

25. The system of claim 19, wherein:
the learn mode includes user interface features further comprising a user-controllable stream mode instruction element usable to designate a stream mode segment that comprises a segment of a part program that is designated for stream mode execution;
the editable part program representation of part program instructions further comprising a stream mode segment representation;
the run mode further comprises a nonstream mode for executing part program instructions that are not in a stream mode segment in addition to the stream mode, that is used for executing part program instructions that are in a stream mode segment;
during the learn mode, the edit mode of execution executes the part program image acquisition instructions and corresponding image analysis instructions of the first plurality of part program instructions to perform the image acquisition operations and corresponding image analysis operations in a manner that is consistent with the first order, regardless of whether or not the first plurality of part program instructions are included in a stream mode segment; and
during the run mode, the stream mode executes the first plurality of part program instructions according to the second order only upon the condition that they are included in a stream mode segment.

26. A method for operating a precision machine vision inspection system comprising an imaging portion, a stage for holding one or more workpieces in a field of view (FOV) of the imaging portion, a control portion including a processor, a display, and a user interface, the method comprising:
providing a learn mode operable to receive user input to control operations of the machine vision inspection system and record instructions corresponding to the controlled operations in order to create a part program, operable to edit a part program, and operable to execute previously recorded part program instructions according to an edit mode of execution, the learn mode including user interface features comprising:
an editable part program representation of part program instructions, comprising image acquisition instruction representations corresponding to image acquisition operations and image analysis instruction representations corresponding to image analysis operations;
providing a run mode operable to execute a previously created part program, the run mode comprising a stream mode for executing part program instructions, wherein the learn mode is configured such that:
the editable part program representation represents a first plurality of part program image acquisition and corresponding image analysis instructions in a first order corresponding to an order in which the corresponding controlled operations were performed to create the part program; and
the edit mode of execution executes the part program image acquisition instructions and corresponding image analysis instructions of the first plurality of part program instructions to perform the image acquisition operations and corresponding image analysis operations in a manner that is consistent with the first order; and
the run mode is configured such that:
the stream mode executes the first plurality of part program instructions according to a second order, the second order comprising:
performing the first plurality of part program image acquisition instructions to perform their corresponding image acquisition operations in a sequential order without dependence on performing the corresponding image analysis operations, and performing the first plurality of part program image analysis instructions to perform their corresponding image analysis operations after their corresponding images are acquired.

27. The method of claim 26, wherein the performance of the image acquisition operations in a sequential order is done during a continuous image acquisition sequence comprising at least one of (a) operations wherein the stage and the imaging portion move continuously relative to one another for acquiring the images, or (b) operations wherein the stage and the imaging portion move approximately continuously relative to one another for acquiring the images except for image acquisition motion operations required to limit image blur at imaging locations, and without motion delays due to image analysis operations.

28. The method of claim 26, wherein the performance of the image analysis operations after their corresponding images are acquired is performed as least partly during the sequential order of image acquisition operations.

29. The method of claim 26, wherein the learn mode is configured such that when a part program that is executed using the stream mode during run mode is recalled for editing, the editable part program representation is displayed in the first order, and the edit mode of execution executes the image acquisition operations and corresponding image analysis operations in a manner that is consistent with the first order.

30. The method of claim 26, wherein the part program that is executed using the stream mode during run mode comprises a first set of instructions and a second set of instructions, the first set of instructions comprising first image acquisition instructions and first image analysis instructions that comprise video tool instructions of a first video tool, and the second set of instructions comprising second image acquisition instructions and second image analysis instructions that comprise video tool instructions of a second video tool, wherein during the edit mode of execution, the first image acquisition instructions and first image analysis instructions that comprise video tool instructions of the first video tool are executed before beginning execution of the second image acquisition instructions and the second image analysis instructions that comprise video tool instructions of the second video tool; and
during the run mode, the part program is executed in the stream mode wherein the first and second image acquisition instructions are executed in a sequential order without dependence on performing the corresponding first and second image analysis operations that comprise video tool instructions of the first and second video tool.

31. The method of claim 30, wherein during the learn mode, the first and second sets of instructions are executed in the first order wherein at least some of the first and second image acquisition instructions are interspersed with the video tool instructions of the first video tool and the second video tool, the instructions being displayed on the user interface in the first order; and during the run mode, the part program instructions are processed to determine an image acquisition sequence or routine that comprises the image acquisition instructions of the first and second sets of instructions but not the video tool instructions, the image acquisition routine is executed for acquiring the images, and while the image acquisition routine is being executed, the video tool instructions are executed.

* * * * *

UNITED STATES PATENT AND TRADEMARK OFFICE
CERTIFICATE OF CORRECTION

PATENT NO. : 9,167,215 B2  
APPLICATION NO. : 14/307458  
DATED : October 20, 2015  
INVENTOR(S) : M. Delaney et al.

Page 1 of 1

It is certified that error appears in the above-identified patent and that said Letters Patent is hereby corrected as shown below:

In the claims

| COLUMN | LINE | |
|---|---|---|
| 22 | 29 | Claim 3, change "as least partly" to -- at least partly -- |
| 26 | 27 | Claim 21, change "as least partly" to -- at least partly -- |
| 28 | 30 | Claim 28, change "as least partly" to -- at least partly -- |

Signed and Sealed this  
Twenty-sixth Day of July, 2016

Michelle K. Lee  
*Director of the United States Patent and Trademark Office*